United States Patent [19]
Bemis et al.

[11] Patent Number: 6,162,790
[45] Date of Patent: Dec. 19, 2000

[54] INHIBITORS OF INTERLEUKIN-1β CONVERTING ENZYME

[75] Inventors: Guy W. Bemis, Arlington; John P. Duffy, Brighton, both of Mass.; Wolf Herman Fridman, Paris, France; Julian M. C. Golec, Swindon, United Kingdom; David J. Livingston, Newtonville, Mass.; Michael D. Mullican, Needham, Mass.; Mark A. Murcko, Holliston, Mass.; Robert E. Zelle, Stow, Mass.

[73] Assignee: Vertex Pharmaceuticals Incorporated, Cambridge, Mass.

[21] Appl. No.: 09/024,537

[22] Filed: Feb. 17, 1998

Related U.S. Application Data

[62] Division of application No. 08/575,648, Dec. 20, 1995, Pat. No. 5,843,904.

[51] Int. Cl.[7] ................................................ A61K 38/00
[52] U.S. Cl. .......................... 514/18; 514/19; 530/330; 530/331
[58] Field of Search ........................... 530/331; 514/18, 514/19

[56] References Cited

U.S. PATENT DOCUMENTS

| | | | |
|---|---|---|---|
| 4,276,298 | 6/1981 | Jones et al. | 424/270 |
| 4,369,183 | 1/1983 | Jones et al. | 424/263 |
| 4,499,295 | 2/1985 | Mueller et al. | 560/53 |
| 4,551,279 | 11/1985 | Mueller et al. | 260/404 |
| 4,584,397 | 4/1986 | Mueller et al. | 560/75 |
| 4,968,607 | 11/1990 | Dower et al. | 435/69.1 |
| 5,008,245 | 4/1991 | Digenis et al. | 514/18 |
| 5,055,451 | 10/1991 | Krantz et al. | 514/19 |
| 5,081,228 | 1/1992 | Dower et al. | 530/35.1 |
| 5,158,936 | 10/1992 | Krantz et al. | 514/19 |
| 5,180,812 | 1/1993 | Dower et al. | 530/351 |
| 5,374,623 | 12/1994 | Zimmerman et al. | 514/17 |
| 5,411,985 | 5/1995 | Bills et al. | 514/460 |
| 5,416,013 | 5/1995 | Black et al. | 435/226 |
| 5,430,128 | 7/1995 | Chapman et al. | 530/330 |
| 5,434,248 | 7/1995 | Chapman et al. | 530/330 |
| 5,462,939 | 10/1995 | Dolle et al. | 514/231.5 |
| 5,486,623 | 1/1996 | Zimmerman et al. | 549/417 |
| 5,498,616 | 3/1996 | Mallamo et al. | 514/300 |
| 5,498,695 | 3/1996 | Daumy et al. | 530/331 |
| 5,527,882 | 6/1996 | Mitchell et al. | 530/328 |
| 5,552,400 | 9/1996 | Dolle et al. | 514/221 |
| 5,565,430 | 10/1996 | Dolle et al. | 514/19 |
| 5,843,904 | 12/1998 | Bemis et al. | 514/18 |

FOREIGN PATENT DOCUMENTS

| | | | |
|---|---|---|---|
| 64514/94 | 12/1994 | Australia | C07F 9/32 |
| 0 275 101 | 7/1988 | European Pat. Off. | C07K 5/02 |
| 0 410 411 | 1/1991 | European Pat. Off. | C07K 5/04 |
| 0 417 721 | 3/1991 | European Pat. Off. | C07K 5/10 |
| 0 479 489 | 4/1992 | European Pat. Off. | C07K 5/08 |
| 0 504 938 | 9/1992 | European Pat. Off. | A61K 37/02 |
| 0 519 748 | 12/1992 | European Pat. Off. | C07K 5/04 |
| 0 525 420 | 2/1993 | European Pat. Off. | C07D 307/56 |
| 0 528 487 | 2/1993 | European Pat. Off. | C07K 5/10 |
| 0 529 713 | 3/1993 | European Pat. Off. | B01J 20/32 |
| 0 533 226 | 3/1993 | European Pat. Off. | C07K 5/10 |
| 0 533 350 | 3/1993 | European Pat. Off. | C12N 15/57 |
| 0 618 223 | 10/1994 | European Pat. Off. | C07K 5/02 |
| 0 623 606 | 11/1994 | European Pat. Off. | C07D 307/60 |
| 0 628 550 | 12/1994 | European Pat. Off. | C07D 237/24 |
| 0 644 197 | 3/1995 | European Pat. Off. | C07K 5/02 |
| 0 644 198 | 3/1995 | European Pat. Off. | C07K 5/02 |
| WO 90/13549 | 11/1990 | WIPO | C07D 417/06 |
| WO 91/15577 | 10/1991 | WIPO | C12N 9/64 |
| WO 93/05071 | 3/1993 | WIPO | C07K 13/00 |
| WO 93/09135 | 5/1993 | WIPO | C07K 5/04 |
| WO 93/14777 | 8/1993 | WIPO | A61K 37/00 |
| WO 93/16710 | 9/1993 | WIPO | A61K 37/00 |
| WO 93/25683 | 12/1993 | WIPO | C12N 15/12 |
| WO 93/25685 | 12/1993 | WIPO | C12N 15/12 |
| WO 93/25694 | 12/1993 | WIPO | C12N 15/57 |
| WO 94/00154 | 1/1994 | WIPO | A61K 39/395 |
| WO 94/03480 | 2/1994 | WIPO | C07K 5/02 |
| WO 95/00160 | 1/1995 | WIPO | A61K 37/02 |
| WO 95/05192 | 2/1995 | WIPO | A61K 38/06 |
| WO 95/16706 | 6/1995 | WIPO | C07K 14/54 |
| WO 95/26958 | 10/1995 | WIPO | C07D 239/47 |
| WO 95/29672 | 11/1995 | WIPO | A61K 31/16 |
| WO 95/33751 | 12/1995 | WIPO | C07D 487/04 |
| WO 96/03982 | 2/1996 | WIPO | A61K 31/15 |

OTHER PUBLICATIONS

M. Ator, "Peptide and Non–peptide Inhibitors of Interleukin–1β Converting Enzyme", *Cambridge Healthtech Institute (Inflammatory Cytokine Antagonists Targets, Strategies and Indication)*, (1994).

M.A. Ator and R.E. Dolle, "Interleukin–1β Converting Enzyme: Biology and the Chemistry of Inhibitors", *Curr. Pharm. Design*, 1, pp. 191–210 (1995).

M. Baringa, "Death Gives Birth to the Nervous System. But How?", *Science*, 259, pp. 762–763 (1993).

P. Bender & J. Lee, "Pharmacological Modulation of Interleukin–1", *Annu. Rep. Med. Chem.*, 25, pp. 185–193 (1989).

R. Black et al., "Activation of Interleukin–1β by a Co–induced Protease", *FEBS Lett.*, 247, pp. 386–390 (1989).

(List continued on next page.)

*Primary Examiner*—Bennett Celsa
*Attorney, Agent, or Firm*—Fish & Neave; James F. Haley, Jr.; Lisa A. Dixon

[57] ABSTRACT

The present invention relates to novel classes of compounds which are inhibitors of interleukin-1 β converting enzyme. This invention also relates to pharmaceutical compositions comprising these compounds. The compounds and pharmaceutical compositions of this invention are particularly well suited for inhibiting ICE activity and consequently, may be advantageously used as agents against interleukin-1 and apoptosis-mediated diseases, including inflammatory diseases, autoimmune diseases, proliferative, infectious, and degenerative diseases. This invention also relates to methods for inhibiting ICE activity and methods for treating interleukin-1 mediated diseases using the compounds and compositions of this invention.

16 Claims, No Drawings-

OTHER PUBLICATIONS

J. Breitner et al., "Inverse Association of Anti–inflammatory Treatments and Alzheimer's Disease: Initial Results of a Co–twin Control Study", *Neurology*, 44, pp. 227–232 (1994).

F. Casano et al., "The Structure and Complete Nucleotide Sequence of the Murine Gene Encoding Interleukin–1β Converting Enzyme (ICE)", *Genomics*, 20, pp. 474–481 (1994).

D. Cerretti et al., "Molecular Cloning of the Interleukin–1β Converting Enzyme", *Science*, 256, pp. 97–100 (1992).

K. Chapman, "Synthesis of a Potent, Reversible Inhibitor of Interleukin–1β Converting Enzyme", *Bioorg. Med. Chem. Lett.*, 2, pp. 613–618 (1992).

C. Dinarello, "Role of Interleukin–1 in Infectious Diseases", *Immunol. Rev.*, 127, pp. 119–146 (1992).

C. Dinarello et al., "Anticytokine Strategies in the Treatment of the Systemic Inflammatory Response Syndrome", *J. Am. Med. Assoc.*, 269, pp. 1829–1835 (1993).

R. Dolle et al., "Aspartyl α–((1–Phenyl–3–(trifluoromethyl)–pyrazole–5–yl)oxy) methyl Ketones as Interleukin–1β Converting Enzyme Inhibitors. Significance of the $P_1$ and $P_3$ Amido Nitrogens for Enzyme–Peptide Inhibitor Binding", *J. Med. Chem.*, 37, pp. 3863–3865 (1994).

R. Dolle et al., "Aspartyl α–((Diphenylphosphinyl)oxy)methyl Ketones as Novel Inhibitors of Interleukin–1β Converting Enzyme. Utility of the Diphenylphosphinic Acid Leaving Group for the Inhibition of Cysteine Proteases", *J. Med. Chem.*, 38, pp. 220–222 (1995).

R. Dolle et al., "$P_1$ Aspartate–Based Peptide α–((2, 6–Dichlorobenzoyl)oxy)methyl Ketones as Potent Time–Dependent Inhibitors of Interleukin–1β–Converting Enzyme", *J. Med. Chem.*, 37, pp. 563–564 (1994).

P. Edwards et al., "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole", *J. Am. Chem. Soc.*, 114, pp. 1854–1863 (1992).

T. Fan et al., "Stimulation of Angiogenesis by Substance P and Interleukin–1 in the Rat and Its Inhibition by $NK_1$ or Interleukin–1 Receptor Antagonists", *Br. J. Pharmacol.*, 110, pp. 43–49 (1993).

I. Fauszt et al., "Inhibition of Interleukin–1β Converting Enzyme by Peptide Derivatives", *Proc. of the 13th Am. Peptide Symp.*, Jun. 20–25, 1993, Hodges, R.S. and Smith, J.A., Eds., *Peptides*, pp. 589–591 (1994).

D.S. Fletcher et al., "A Synthetic Inhibitor of Interleukin–1β Converting Enzyme Prevents Endotoxin–Induced Interleukin–1β Production In Vitro and In Vivo", *J. Interfer. Cytokine Res.*, 15, pp. 243–248 (1995).

V. Gagliardini et al., "Prevention of Vertebrate Neuronal Death by the crmA Gene", *Science*, 263, pp. 826–828 (1994).

T. Geiger et al., "Neutralization of Interleukin–1β Activity in vivo with a Monoclonal Antibody Alleviates Collagen–induced Arthritis in DBA/1 Mice and Prevents the Associated Acute–phase Response", *Clin. Exp. Rheumatol.*, 11, pp. 515–522 (1993).

T. Graybill et al., "The Preparation and Evaluation of Peptidic Aspartyl Hemiacetals as Reversible Inhibitors of ICE", *Am. Chem. Soc. Abs. (206th Natl. Mtg.)*, MEDI 235 (1993).

T. Graybill et al., "Preparation and evaluation of peptidic aspartyl hemiacetals as reversible inhibitors of interleukin–1β converting enzyme (ICE)", *Int. J. Peptide Protein Res.*, 44, pp. 173–182 (1994).

T. Graybill et al., "Synthesis and Evaluation of Diacylhydrazines as Inhibitors of the Interleukin–1β Converting Enzyme (ICE)", *Bioorg. Med. Chem. Lett.*, 5, pp. 1197–1202 (1995).

W. Griffin et al., "Brain Interleukin 1 and S–100 Immunoreactivity are Elevated in Down Syndrome and Alzheimer Disease", *Proc. Natl. Acad. Sci. USA*, 86, pp. 7611–7615 (1989).

C. Hammerberg et al., "Interleukin–1 Receptor Antagonist in Normal and Psoriatic Epidermis", *J. Clin. Invest.*, 90, pp. 571–583 (1992).

S. Hanessian et al., "Design and Synthesis of a Prototype Model Antagonist of Tachykinin NK–2 Receptor", *Biorg. Med. Chem. Lett.*, 3, pp. 2689–2692 (1993).

E. Harris, "Rheumatoid Arthritis: Pathophysiology and Implications for Therapy", *N. Eng. J. Med.*, 322, pp. 1277–1289 (1990).

A. Howard et al., "High–Level Production and Characterization of Functional Human Interleukin–1β Converting Enzyme in Baculovirus and *E. coli* Expression Systems", *J. Cell. Biochem. Suppl.*, 17B, p. 146 (1993).

A. Howard et al., "Human Interleukin–1β Converting Enzyme: A Mutational Analysis of Proenzyme Activation", *J. Cell. Biochem. Suppl.*, 17B, p. 113 (1993).

A. Howard et al., "IL–1–Converting Enzyme Requires Aspartic Acid Residues for Processing of the IL–1β Precursor at Two Distinct Sites and Does Not Cleave 31–kDa IL–1α", *J. Immunol.*, 147, pp. 2964–2969 (1991).

I. Kamphuis et al., "Thiol Proteases: Comparative Studies Based on the High–resolution Structures of Papain and Actinidin, and on Amino Acid Sequence Information for Cathepsins B and H, and Stem Bromelain", *J. Mol. Biol.*, 182, pp. 317–329 (1985).

M. Kostura et al., "Identification of a Monocyte Specific Pre–Interleukin 1β Convertase Activity", *Proc. Natl. Acad. Sci. USA*, 86, pp. 5227–5231 (1989).

K. Kuida et al., "Altered Cytokine Export and Apoptosis in Mice Deficient in Interleukin–1β Converting Enzyme", *Science*, 267, pp. 2000–2003 (1995).

P. Li et al., "Mice Deficient in IL–1β–Converting Enzyme are Defective in Production of Mature IL–1β and Resistant to Endotoxic Shock", *Cell*, 80, pp. 401–411 (1995).

C. Lipinski, "Bioisosterism in Drug Design", *Annu. Rep. Med. Chem.*, 21, pp. 283–291 (1986).

G. Lonnemann et al., "Differences in the Synthesis and Kinetics of Release of Interleukin 1α, Interleukin 1β and Tumor Necrosis Factor from Human Mononuclear Cells", *Eur. J. Immunol.*, 19, pp. 1531–1536 (1989).

A. MacKenzie et al., "An Inhibitor of the Interleukin–1β–Processing Enzyme Blocks IL–1 Release and Reduces Pyrexia and Acute Inflammation", *Inflammation Research Association (7th Internat. Conf.)*, W42 (1994).

T. Mandrup–Poulsen et al., "Involvement of Interleukin 1 and Interleukin 1 Antagonist in Pancreatic β–Cell Destruction in Insulin–dependent Diabetes Mellitus", *Cytokine*, 5, pp. 185–191 (1993).

C. March et al., "Cloning, Sequence and Expression of Two Distinct Human Interleukin–1 Complementary DNAs", *Nature*, 315, pp. 641–647 (1985).

J. Marx, "Cell Death Studies Yield Cancer Clues", *Science*, 259, pp. 760–761 (1993).

D. Miller et al., "The IL–1β Converting Enzyme as a Therapeutic Target", *Ann. N.Y. Acad. Sci.,* 696, pp. 133–148 (1993).

B. Miller et al., "Inhibition of Mature IL–1β Production in Murine Macrophages and a Murine Model of Inflammation by WIN 67694, an Inhibitor of IL–1β Converting Enzyme", *J. Immunol.,* 154, pp. 1331–1338 (1995).

M. Miura et al., "Induction of Apoptosis in Fibroblasts by IL–1β–Converting Enzyme, a Mammalian Homolog of the *C. elegans* Cell Death Gene ced–3", *Cell,* 75, pp. 653–660 (1993).

A. Mjalli et al., "Phenylalkyl Ketones as Potent Reversible Inhibitors of Interleukin–1β Converting Enzyme", *Bioorg. Med. Chem. Lett.,* 3, pp. 2689–2692 (1993).

A. Mjalli et al., "Activated Ketones as Potent Reversible Inhibitors of Interleukin–1β Converting Enzyme", Bioorg. Med. Chem. Lett., 4, pp. 1965–1968 (1994).

S. Molineaux et al., "Interleukin 1β (IL–1β) Processing in Murine Macrophages Requires a Structurally Conserved Homologue of Human IL–1β Converting Enzyme", *Proc. Natl. Acad. Sci. USA,* 90, pp. 1809–1813 (1993).

B. Mosley et al., "Determination of the Minimum Polypeptide Lengths of the Functionally Active Sites of Human Interleukins 1α and 1β", *Proc. Natl. Acad. Sci. USA,* 84, pp. 4572–4576 (1987).

M. Mullican et al., "The Synthesis and Evaluation of Peptidyl Aspartyl Aldehydes as Inhibitors of ICE", *Bioorg. Med. Chem. Lett.,* 4, pp. 2359–2364 (1994).

C. Nalin, "Apoptosis Research Enters the ICE Age", *Structure,* 3, pp. 143–145 (1995).

M. Nett et al., "Molecular Cloning of the Murine IL–1β Converting Enzyme cDNA", *J. Immunol.,* 149, pp. 3254–3259 (1992).

M. Nett–Fiordalisi et al., "Characterization and Activation of the Murine Interleukin–1β (IL–1β) Converting Enzyme", *J. Cell. Biochem. Suppl.,* 17B, p. 117 (1993).

I. Noronha et al., "In situ Production of TNF–α, IL–1β and IL–2R in ANCA–positive Glomerulonephritis", *Kidney Int.,* 43, pp. 682–692 (1993).

K. Ohlsson et al., "Interleukin–1 Receptor Antagonist Reduces Mortality from Endotoxin Shock", *Nature,* 348, pp. 550–552 (1990).

J. Oppenheim et al., "There is More than One Interleukin 1", *Immunol. Today,* 7, pp. 45–55 (1986).

M. Pennington & N. Thornberry, "Synthesis of a Fluorogenic Interleukin–1β Converting Enzyme Substrate Based on Resonance Energy Transfer", *Pept. Res.,* 7, pp. 72–76 (1994).

L. Polgár, "On the Mode of Activation of the Catalytically Essential Sulfhydryl Group of Papain", *Eur. J. Biochem.,* 33, pp. 104–109 (1973).

C. Prasad et al., "$P_1$ Aspartate–Based Peptide α–Arylacyloxy– and α–Aryloxymethyl Ketones as Potent Time–Dependent Inhibitors of Interleukin 1β Converting Enzyme", *Am. Chem. Soc. Abs.* (*24th Med. Chem. Symp.*), 66 (1994).

C. Ray et al., "Viral Inhibition of Inflammation: Cowpox Virus Encodes an Inhibitor of the Interleukin–1β Converting Enzyme", *Cell,* 69, pp. 597–604 (1992).

L. Reiter, "Peptidic p–Nitroanilide Substrates of Interleukin–1β–Converting Enzyme", *Int. J. Pept. Protein Res.,* 43, pp. 87–96 (1994).

L. Revesz et al., "Synthesis of P1 Aspartate–Based Peptide Acyloxymethyl and Fluoromethyl Ketones as Inhibitors of Interleukin–1β–Converting Enzyme", *Tetrahedron Lett.,* 35, pp. 9693–9696 (1994).

R. Robinson and K. Donahue, "Synthesis of a Peptidyl Difluoro Ketone Bearing the Aspartic Acid Side Chain: An Inhibitor of Interleukin–1β Converting Enzyme", *J. Org. Chem.,* 57, pp. 7309–7314 (1992).

M. Salvatore et al., "L–741,494, A Fungal Metabolite that is an Inhibitor of Interleukin–1β Converting Enzyme", *J. Nat. Prods.,* 57, pp. 755–760 (1994).

J. Sandberg et al., "Treatment with an Interleukin–1 Receptor Antagonist Protein Prolongs Mouse Islet Allograft Survival", *Diabetes,* 42, pp. 1845–1851 (1993).

S. Schmidt et al., "Synthesis and Evaluation of Aspartyl α–Chloro–, α–Aryloxy–, and α–Arylacyloxy–methyl Ketones as Inhibitors of Interleukin–1β Converting Enzyme", *Am. Chem. Soc. Abs.* (*208th Natl. Mtg.*), MEDI 4, (1994).

B. Shivers et al., "Molecular Cloning of Rat Interleukin–1β–Converting Enzyme: Distribution and Regulation", *J. Cell. Biochem. Suppl.,* 17B, p. 119 (1993).

I. Singer et al., "Interleukin 1β is Localized in the Cytoplasmic Ground Substance but is Largely Absent from the Golgi Apparatus and Plasma Membranes of Stimulated Human Monocytes", *J. Exp. Med.,* 167, pp. 389–407 (1988).

P. Sleath et al., "Substrate Specificity of the Protease that Processes Human Interleukin–1β", *J. Biol. Chem.,* 265, pp. 14526–14528 (1990).

N. Thornberry et al., "A Novel Heterodimeric Cysteine Protease is Required for Interleukin–1β Processing in Monocytes", *Nature,* 356, pp. 768–774 (1992).

N. Thornberry et al., "Inactivation of Interleukin–1β Converting Enzyme by Peptide (Acyloxy)methyl Ketones", *Biochemistry,* 33, pp. 3934–3940 (1994).

J. Uhl et al., "Secretion of Human Monocyte Mature IL–1β: Optimization of Culture Conditions and Inhibition by ICE Inhibitors", *Inflammation Research Association* (*7th Internat. Conf.*), W41 (1994).

N.P.C. Walker et al., "Crystal Structure of the Cysteine Protease Interleukin–1β–Converting Enzyme: A $(p20/p10)_2$ Homodimer", *Cell,* 78, pp. 343–352 (1994).

P. Warner, et al., "Pyridone HLE Inhibitors: Variation of the 3 and 5 Substituents", *Royal Soc. Chem. Abs.* (*7th RSC–SCI Med. Chem. Symp.*), P23 (1993).

K.P. Wilson et al., "Structure and Mechanism of Interleukin–1 Converting Enzyme", *Nature,* 370, pp. 270–275 (1994).

P. Wooley et al., "The Effect of an Interleukin–1 Receptor Antagonist Protein on Type II Collagen–induced Arthritis and Antigen–induced Arthritis in Mice", *Arthritis Rheum.,* 36, pp. 1305–1314 (1993).

J. Yuan et al., "The *C.elegans* Cell Death Gene ced–3 Encodes a Protein Similar to Mammalian Interleukin–1β–Converting Enzyme", *Cell,* 75, pp. 641–652 (1993).

INHIBITORS OF INTERLEUKIN-1β CONVERTING ENZYME

This application is a divisional of Ser. No. 08/575,648 Dec. 20, 1995 now U.S. Pat. No. 5,843,904.

TECHNICAL FIELD OF THE INVENTION

The present invention relates to novel classes of compounds which are inhibitors of interleukin-1 β converting enzyme ("ICE"). This invention also relates to pharmaceutical compositions comprising these compounds. The compounds and pharmaceutical compositions of this invention are particularly well suited for inhibiting ICE activity and consequently, may be advantageously used as agents against interleukin-1- ("IL-1") and apoptosis-mediated diseases, including inflammatory diseases, autoimmune diseases, proliferative disorders, infectious diseases, and degenerative diseases. This invention also relates to methods for inhibiting ICE activity and methods for treating interleukin-1- and apoptosis-mediated diseases using the compounds and compositions of this invention.

BACKGROUND OF THE INVENTION

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al, *Immunology Today,* 7, pp. 45–56 (1986). As such, it is involved in the pathogenesis of chronic and acute inflammatory and autoimmune diseases. For example, in rheumatoid arthritis, IL-1 is both a mediator of inflammatory symptoms and of the destruction of the cartilage proteoglycan in afflicted joints. IL-1 is also a highly potent bone resorption agent. It is alternatively referred to as "osteoclast activating factor" in destructive bone diseases such as osteoarthritis and multiple myeloma. Bataille, R. et al., *Int. J. Clin. Lab. Res.,* 21, p. 283 (1992). In certain proliferative disorders, such as acute myelogenous leukemia and multiple myeloma, IL-1 can promote tumor cell growth and adhesion. In these disorders, IL-1 also stimulates production of other cytokines such as IL-6, which can modulate tumor development. Tartour et al., *Cancer Res.* 54, 6243 (1994).

IL-1 is predominantly produced by peripheral blood monocytes as part of the inflammatory response and exists in two distinct agonist forms, IL-1 α and IL-1 β. Mosely, B. S. et al., *Proc. Nat. Acad. Sci.,* 84, pp. 4572–4576 (1987); Lonnemann, G. et al., *Eur. J. Immunol.,* 19, pp. 1531–1536 (1989).

IL-1 β is synthesized as a biologically inactive precursor, pIL-1 β. pIL-1 β lacks a conventional leader sequence and is not processed by a signal peptidase. March, C. J., *Nature,* 315, pp. 641–647 (1985). Instead, pIL-1 β is cleaved by interleukin-1 β converting enzyme ("ICE") between Asp-116 and Ala-117 to produce the biologically active C-terminal fragment found in human serum and synovial fluid. Sleath, P. R., et al., *J. Biol. Chem.,* 265, pp. 14526–14528 (1992); A. D. Howard et al.,*J. Immunol.,* 147, pp. 2964–2969 (1991).

ICE is a cysteine protease localized primarily in monocytes. It converts precursor IL-1 β to the mature form. Black, R. A. et al., *FEBS Lett.,* 247, pp. 386–390 (1989); Kostura, M. J. et al., *Proc. Natl. Acad. Sci. USA,* 86, pp. 5227–5231 (1989). Processing by ICE is also necessary for the transport of mature IL-1 β through the cell membrane. ICE, or its homologues, also appears to be involved in the regulation of cell death or apoptosis. Yuan, J. et al., *Cell,* 75, pp. 641–652 (1993); Miura, M. et al., *Cell,* 75, pp. 653–660 (1993); Nett-Fiordalisi, M. A. et al., *J. Cell Biochem.,* 17B, p. 117 (1993). In particular, ICE or ICE homologues are thought to be associated with the regulation of apoptosis in neurodegenerative diseases, such as Alzheimer's and Parkinson's disease. Marx, J. and M. Baringa, *Science,* 259, pp. 760–762 (1993); Gagliardini, V. et al., *Science,* 263, pp. 826–828 (1994).

ICE has been demonstrated to mediate apoptosis (programmed cell death) in certain tissue types. Steller, H., *Science,* 267, p. 1445 (1995); Whyte, M. and Evan, G., *Nature,* 376, p. 17 (1995); Martin, S. J. and Green, D. R., *Cell,* 82, p. 349 (1995); Alnemri, E. S., et al.,*J. Biol. Chem.,* 270, p. 4312 (1995); Yuan, J. *Curr. Opin. Cell Biol.,* 7, p. 211 (1995). Therapeutic applications for inhibition of apoptosis may include treatment of Alzheimer's disease, Parkinson's disease, stroke, myocardial infarction, spinal atrophy, and aging. A transgenic mouse with a disruption of the ICE gene is deficient in Fas-mediated apoptosis. Kuida, et al. (1995). This activity of ICE is distinct from its role as the processing enzyme for pro-IL-1 β. It is conceivable that in certain tissue types, inhibition of ICE may not affect secretion of mature IL-1 β, but may inhibit apoptosis.

ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., *Nature,* 356, pp. 768–774 (1992). The ICE proenzyme has been divided into several functional domains: a rag prodomain (p14), a p22/20 subunit, a polypeptide linker and a p10 subunit. Thornberry *et al., supra;* Casano et al., *Genomics,* 20, pp. 474–481 (1994).

Full length p45 has been characterized by its cDNA and amino acid sequences. PCT patent applications WO 91/15577 and WO 94/00154. The p20 and p10 cDNA and amino acid sequences are also known. Thornberry *et al., supra.* Murine and rat ICE have also been sequenced and cloned. They have high amino acid and nucleic acid sequence homology to human ICE. Miller, D. K. et al.,*Ann. N.Y. Acad. Sci.,* 696, pp. 133–148 (1993); Molineaux, S. M. et al., *Proc. Nat. Acad. Sci.,* 90, pp. 1809–1813 (1993). The three-dimensional structure of ICE has been determined at atomic resolution by X-ray crystallography. Wilson, K. P., et al., *Nature,* 370, pp. 270–275 (1995). The active enzyme exists as a tetramer of two p20 and two p10 subunits.

Additionally, there exist human homologs of ICE with sequence similarities in the active site regions of the enzymes. Such homologs include TX (or $ICE_{rel-II}$ or ICH-2) (Faucheu, et al., *EMBO J.,* 14, p. 1914 (1995); Kamens J., et al.,*J. Biol. Chem.,* 270, p. 15250; Nicholson et al.,*J. Biol. Chem.,* 270 15870 (1995)), TY (or $ICE_{rel-III}$) (Nicholson et al.,*J. Biol. Chem.,* 270, p. 15870 (1995)), ICH-1 (or Nedd-2) (Wang, L. et al., *Cell,* 78, p. 739 (1994)), MCH-2, (Fernandes-Alnemri, T. et al., *Cancer Res.,* 55, p. 2737 (1995), CPP32 (or YAMA or apopain). Fernandes-Alnemri, T. et al.,*J. Biol. Chem.,* 269, p. 30761 (1994); Nicholson, D. W. et al., *Nature,* 376, p. 37 (1995)), and CMH-1 (or MCH-3) (Lippke, et al., *J. Biol Chem.,* (1996); Fernandes-Alnemri, T. et al., *Cancer Res.,* (1995)). Each of these ICE homologs, as well as ICE itself, is capable of inducing apoptosis when overexpressed in transfected cell lines. Inhibition of one or more of these homologs with the peptidyl ICE inhibitor Tyr-Val-Ala-Asp-chloromethylketone results in inhibition of apoptosis in primary cells or cell lines.

Lazebnik et al., Nature, 371, p. 346 (1994). The compounds described herein are also capable of inhibiting one or more homologs of ICE (see example). Therefore, one can envisage using these compounds to inhibit apoptosis in tissue types that contain ICE homologs, but which do not contain active ICE or produce mature IL-1 β.

ICE inhibitors represent a class of compounds useful for the control of inflammation or apoptosis or both. Peptide and peptidyl inhibitors of ICE have been described. PCT patent applications WO 91/15577; WO 93/05071; WO 93/09135; WO 93/14777 and WO 93/16710; and European patent application 0 547 699. Such peptidyl inhibitors of ICE have been observed to block the production of mature IL-1 β in a mouse model of inflammation (Ku, et al. or vide infra) and to suppress growth of leukemia cells in vitro (Estrov, et al., Blood, 84, p. 380a (1994)).

Accordingly, the need exists for compounds that can effectively inhibit the action of ICE in vivo, for use as agents for preventing and treating chronic and acute forms of IL-1-mediated diseases, apoptosis-mediated diseases, as well as inflammatory, autoimmune, bone-destructive, proliferative, infectious, degenerative, or necrotic diseases.

SUMMARY OF THE INVENTION

The present invention provides novel classes of compounds, and pharmaceutically acceptable derivatives thereof, that are useful as inhibitors of ICE. These compounds can be used alone or in combination with other therapeutic or prophylactic agents, such as antibiotics, immunomodulators or other anti-inflammatory agents, for the treatment or prophylaxis of diseases mediated by IL-1 or by apoptosis. According to a preferred embodiment, the compounds of this invention are capable of binding to the active site of ICE and inhibiting the activity of that enzyme.

It is a principal object of this invention to provide novel classes of inhibitors of ICE represented by formulas:

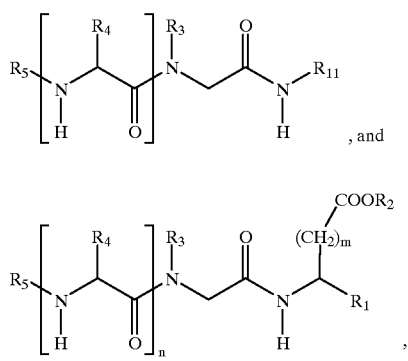

wherein the various substituents are described herein.

ABBREVIATIONS AND DEFINITIONS

| Designation | Abbreviations Reagent or Fragment |
|---|---|
| Ala | alanine |
| Arg | arginine |
| Asn | asparagine |
| Asp | aspartic acid |
| Cys | cysteine |

-continued
ABBREVIATIONS AND DEFINITIONS

| Designation | Abbreviations Reagent or Fragment |
|---|---|
| Gln | glutamine |
| Glu | glutamic acid |
| Gly | glycine |
| His | histidine |
| Ile | isoleucine |
| Leu | leucine |
| Lys | lysine |
| Met | methionine |
| Phe | phenylalanine |
| Pro | proline |
| Ser | serine |
| Thr | threonine |
| Trp | tryptophan |
| Tyr | tyrosine |
| Val | valine |
| $Ac_2O$ | acetic anhydride |
| n-BU | normal-butyl |
| DMF | dimethylformamide |
| DIEA | N,N-diisopropylethylamine |
| EDC | 1-(3-Dimethylaminopropyl)-3-ethylcarbodiimide hydrochloride |
| $Et_2O$ | diethyl ether |
| EtOAc | ethyl acetate |
| Fmoc | 9-fluorenylmethyoxycarbonyl |
| HBTU | O-benzotriazol-1-yl-N,N,N',N'-tetramethyluronium hexafluorophosphate |
| HOBT | 1-hydroxybenzotriazole hydrate |
| MeOH | methanol |
| TFA | trifluoroacetic acid |

DEFINITIONS

The following terms are employed herein:

The term "active site" refers to any or all of the following sites in ICE: the substrate binding site, the site where an inhibitor binds and the site where the cleavage of substrate occurs.

The term "alkenyl", alone or in combination, refers to a straight-chain or branched-chain alkenyl radical containing from 2 to 10, carbon atoms. Examples of such radicals include, but are not limited to, ethenyl, E- and Z-propenyl, isopropenyl, E- and Z-butenyl, E- and Z-isobutenyl, E- and Z-pentenyl, decenyl and the like.

The term "alkynyl", alone or in combination, refers to a straight-chain or branched-chain alkynyl radical containing from 2 to 10, carbon atoms. Examples of such radicals include, but are not limited to, ethynyl (acetylenyl), propynyl, propargyl, butynyl, hexynyl, decynyl and the like.

The term "substitute" refers to the replacement of a hydrogen atom in a compound with a substituent group.

The term "$K_i$" refers to a numerical measure of the effectiveness of a compound in inhibiting the activity of a target enzyme such as ICE. Lower values of $K_i$ reflect higher effectiveness. The $K_i$ value is a derived by fitting experimentally determined rate data to standard enzyme kinetic equations (see I. H. Segel, Enzyme Kinetics, Wiley-Interscience, 1975).

The term "patient" as used in this application refers to any mammal, especially humans.

The term "pharmaceutically effective amount" refers to an amount effective in treating or ameliorating an IL-1- or apoptosis-mediated disease in a patient. The term "prophylactically effective amount" refers to an amount effective in preventing or substantially lessening IL-1- or apoptosis-mediated disease in a patient.

The term "pharmaceutically acceptable carrier or adjuvant" refers to a non-toxic carrier or adjuvant that may be administered to a patient, together with a compound of this invention, and which does not destroy the pharmacological activity thereof.

The term "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an anti-ICE active metabolite or residue thereof.

Pharmaceutically acceptable salts of the compounds of this invention include, for example, those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and $N-(C_{1-4}\ alkyl)_4^+$ salts.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The ICE inhibitors of this invention may contain one or more "asymmetric" carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or configuration. Although specific compounds and scaffolds exemplified in this application may be depicted in a particular stereochemical configuration, compounds and scaffolds having either the opposite stereochemistry at any given chiral center or mixtures thereof are also envisioned.

The ICE inhibitors of this invention may comprise structures which may optionally be substituted at carbon, nitrogen or other atoms by various substituents. Such structures may be singly or multiply substituted. Preferably, the structures contain between 0 and 3 substituents. When multiply substituted, each substituent may be picked independently of any other substituent as long as the combination of substituents results in the formation of a stable compound.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

DETAILED DESCRIPTION OF THE INVENTION

In order that the invention herein described may be more fully understood, the following detailed description is set forth.

The ICE inhibitors of one embodiment (A) of this invention are those of formula (α):

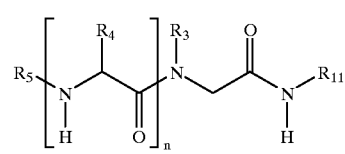

α wherein:
n=0, 1, or 2;
$R_{11}$ is:

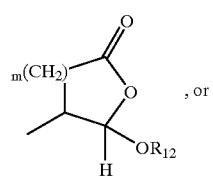

(a)

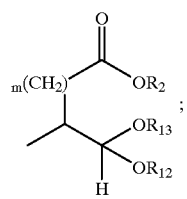

(b)

m is 1 or 2;

$R_{12}$ and $R_{13}$ are independently selected from the group consisting of —$R_7$, —C(O)—$R_7$, and —C(O)—N(H)—$R_7$, or $R_{12}$ and $R_{13}$ taken together form a 4–8-membered saturated cyclic group;

$R_2$ is —H or a —$C_{1-6}$ straight or branched alkyl group optionally substituted with Ar, —OH, —$OR_7$, —C(O)—OH, C(O)—$NH_2$, or —$OR_5$;

$R_7$ is selected from the group consisting of —Ar, a —$C_{1-6}$ straight or branched alkyl group optionally substituted with —Ar, a —$C_{1-6}$ straight or branched alkenyl group optionally substituted with Ar, and a —$C_{2-6}$ straight or branched alkynyl group optionally substituted with Ar;

$R_5$ is selected from the group consisting of:
—C(O)—$R_7$,
—C(O)—$OR_9$,
—C(O)—N($R_9$) ($R_{10}$),
—S(O)$_2$—$R_7$,
—C(O) C (O)—$R_7$,
—$R_7$, and
—H;

each Ar is a cyclic group independently selected from the set consisting of phenyl, 1-naphthyl, 2-naphthyl, indenyl, azulenyl, fluorenyl and anthracenyl and a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyI, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, peridinyl, carbazolyl, acridinyl, phenazinyl, phenothiazinyl and phenoxazinyl, and the aromatic group is optionally singly or multiply substituted with —F, —Cl, —Br, —I, —OR$_{14}$, —NO$_2$, —S(O$_2$)—N(R$_9$) (R$_{10}$), —C(O)—N(R$_9$) (R$_{10}$), —N(H)—C(O)—N(R$_9$) (R$_{10}$), —N(R$_9$) (R$_{10}$), —C(O)—OR$_9$, —CF$_3$, —OCF$_3$, a C$_{1-6}$ straight or branched alkyl group, 1,2-methylenedioxy, —CN, or —N(H)C(NR$_9$)N(R$_9$) (R$_{10}$);

each R$_{14}$ is —H or a C$_{1-6}$ straight or branched alkyl group;

each R$_9$ and R$_{10}$ is independently selected from the group consisting of —H, —Ar, and a C$_{1-5}$ straight or branched alkyl group optionally substituted with —Ar;

each R$_4$ is a —C$_{1-5}$ straight or branched alkyl group optionally substituted with —Ar or —W;

W is —OR$_9$, —SR$_9$, —N(H)C(NR$_9$)N(R$_9$) (R$_{10}$), —C(O)—OR$_9$, or —N(R$_9$) (R$_{10}$);

R$_3$ is —CH$_2$Ar or a 5 to 15-membered non-aromatic cyclic group which contains between 1 and 3 rings, and which optionally contains between 0 and 2 endocyclic oxygen atoms, sulfur atoms, or nitrogen atoms, and wherein the cyclic group is optionally fused with Ar;

provided that when —Ar is substituted with a group containing R$_9$ or R$_{10}$ which comprises one or more additional —Ar groups, the —Ar groups are not substituted with a group containing R$_9$ or R$_{10}$;

Preferred compounds of this embodiment are those wherein:

R$_5$ is —C(O)—R$_7$ or —C(O)C(O)—R$_7$;

each R$_4$ is a C$_{1-5}$ straight or branched alkyl group optionally substituted with Ar;

m is 1;

n is 1;

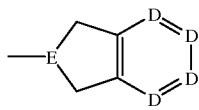

E is CH or N;

each D is independently N or C, wherein C is optionally substituted with —OR$_{14}$, —F, —Cl, —Br, —I, —NO$_2$, —S(O)$_2$—N(R$_9$) (R$_{10}$), —C(O)—N(R$_9$) (R$_{10}$), —N(H)—C(O)—N(R$_9$) (R$_{10}$), —N(R$_9$) (R$_{10}$), —C(O)—OR$_9$, —CF$_3$, —OCF$_3$, a C$_{1-6}$ straight or branched alkyl group, 1,2-methylenedioxy, —CN, or —N(H)C(NR$_9$)N(R$_9$) (R$_{10}$);

each R$_9$ and R$_{10}$ is independently selected from the group consisting of —H, —Ar, and a —C$_{1-5}$ straight or branched alkyl group optionally substituted with —Ar.

The ICE inhibitors of another embodiment of this invention are those of formula (β):

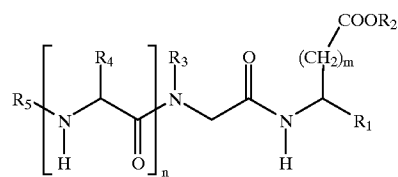

wherein:

m is 1 or 2;

n is 0, 1, or 2;

R$_1$ is selected from the group consisting of:
—CN,
—C(O)—H,
—C(O)—CH$_2$XR$_6$,
—C(O)—CH$_2$F,
—C=N—O—R$_7$, and
—C(O)—R$_8$;

X is selected from the group consisting of O, S, S(O), and S(O)$_2$;

R$_6$ is independently selected from the group consisting of:
—H,
—(CH$_2$)$_p$Ar, and
—C(O)—Ar;

p is 0, 1, 2, or 3;

R$_7$ is selected from the group consisting of —Ar, a —C$_{1-6}$ straight or branched alkyl group optionally substituted with —Ar, a —C$_{1-6}$ straight or branched alkenyl group optionally substituted with Ar, and a —C$_{2-6}$ straight or branched alkynyl group optionally substituted with Ar;

R$_8$ is selected from the following group, in which any ring may optionally be singly or multiply substituted by —NH$_2$, —C(O)—OH, —F, —Cl, —Br, —I, —OH, —NO$_2$, —CN, -perfluoroalkyl C$_{1-3}$ alkyl, —R$_5$, —OR$_5$, —OR$_7$, —N(H)—R$_5$, —N(H)—R$_7$, 1,2-methylenedioxy, and —SR$_7$:

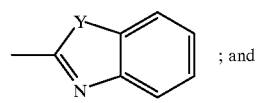; and

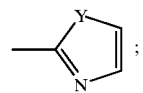;

wherein Y is independently selected from the group consisting of O and S;

each Ar is a cyclic group independently selected from the set consisting of a carbocyclic aromatic group selected from the group consisting of phenyl, 1-naphthyl, 2-naphthyl, indenyl, azulenyl, fluorenyl and anthracenyl and a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzol[b]furanyl, benzo[b]

thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, peridinyl, carbazolyl, acridinyl, phenazinyl, phenothiazinyl and phenoxazinyl, and the cyclic group is optionally being singly or multiply substituted with —$OR_{14}$, —F, —Cl, —Br, —I, —$NO_2$, —$S(O)_2$—N($R_9$) ($R_{10}$), —C(O)—N($R_9$) ($R_{10}$), —N(H)—C(O)—N ($R_9$) ($R_{10}$), —N($R_9$) ($R_{10}$), —C(O)—$OR_9$, —$CF_3$, —$OCF_3$, a $C_{1-6}$ straight or branched alkyl group, 1,2-methylenedioxy, —CN, or —N(H)C(N$R_9$)N($R_9$) ($R_{10}$);

each $R_9$ and $R_{10}$ are independently selected from the group consisting of —H, —Ar, and a —$C_{1-5}$ straight or branched alkyl group optionally substituted with Ar;

each $R_{14}$ is —H or a $C_{1-6}$ straight or branched alkyl group;

$R_5$ is selected from the group consisting of:
—C(O)—$R_7$,
—C(O)—$OR_9$,
—C(O)—N($R_9$) ($R_{10}$),
—$S(O)_2$—$R_7$,
—C(O)C(O)—$R_7$,
—$R_7$, and
—H;

$R_4$ is a —$C_{1-5}$ straight or branched alkyl group optionally substituted with Ar or W;

W is —$OR_9$, —$SR_9$, —N(H)C(N$R_9$)N($R_9$) ($R_{10}$), —C(O)—$OR_9$, and —N$R_9$, ($R_{10}$);

$R_3$ is —$CH_2$Ar or a 5 to 15-membered non-aromatic cyclic group which contains between 1 and 3 rings, and which optionally contains between 0 and 2 endocyclic oxygen atoms, sulfur atoms, or nitrogen atoms, and wherein the cyclic group is optionally fused with Ar;

$R_2$ is —H, or a $C_{1-6}$ straight or branched alkyl group, wherein the alkyl group is optionally substituted with Ar, —OH, —$OR_7$, —C(O)—OH, C(O)—$NH_2$, or —$OR_5$;

provided that when —Ar is substituted with a group containing $R_9$ or $R_{10}$ which comprises one or more additional —Ar groups, the —Ar groups are not substituted with a group containing $R_9$ or $R_{10}$;

Preferred compounds of this embodiment are those wherein:

$R_1$ is —C(O)—H;
$R_5$ is —C(O)—$R_7$ or —C(O)C(O)—$R_7$;
$R_4$ is a —$C_{1-5}$ straight or branched alkyl group optionally substituted by —Ar;
m is 1;
n is 1;

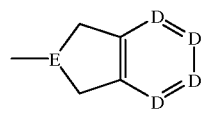

E is CH or N;
each D is independently N or C, wherein C is optionally substituted with —$OR_{14}$, —F, —Cl, —Br, —I, —$NO_2$, —$S(O)_2$—N($R_9$) ($R_{10}$), —C(O)—N($R_9$) ($R_{10}$), —N(H)—C(O)—N($R_9$) ($R_{10}$), —N($R_9$) ($R_{10}$), —C(O)—$OR_9$, —$CF_3$, —$OCF_3$, a $C_{1-6}$ straight or branched alkyl group, 1,2-methylenedioxy, —CN, or —N(H)C(N$R_9$)N($R_9$) ($R_{10}$);

each $R_9$ and $R_{10}$ is independently selected from the group consisting of —H, —Ar, and a —$C_{1-5}$ straight or branched alkyl group optionally substituted with —Ar.

Preferred compounds of this embodiment include but are not limited to:

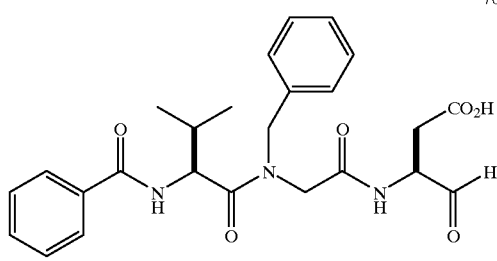

706

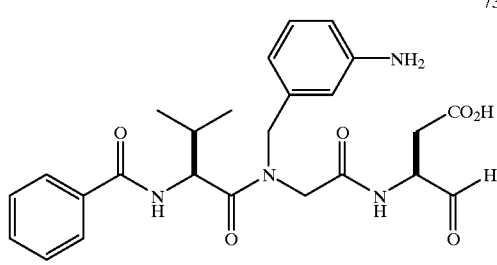

737

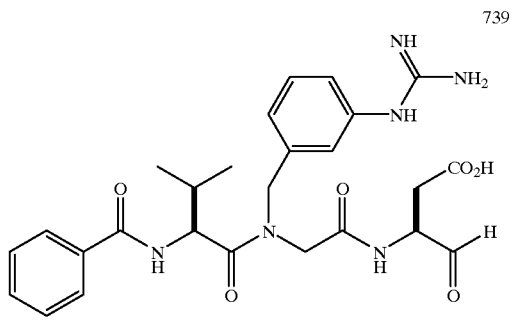

739

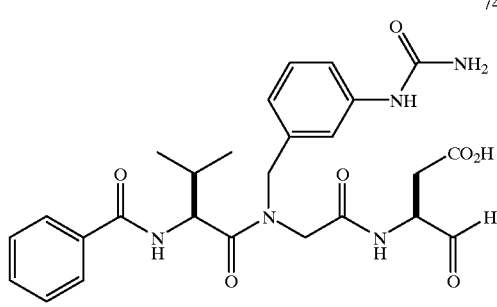

741

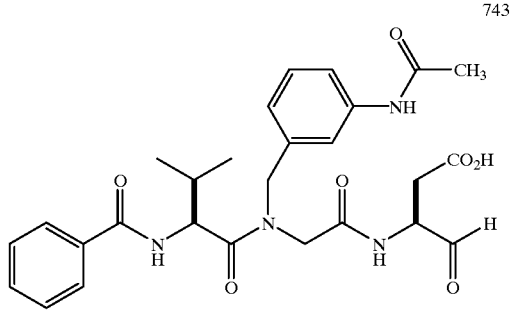

743

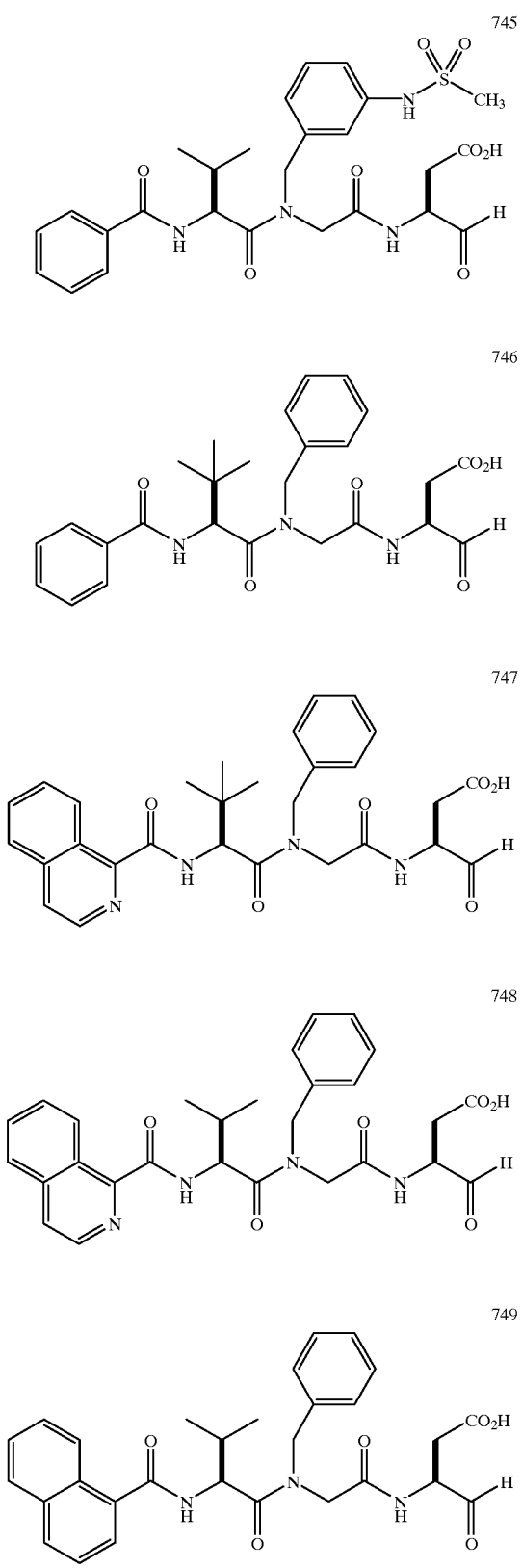
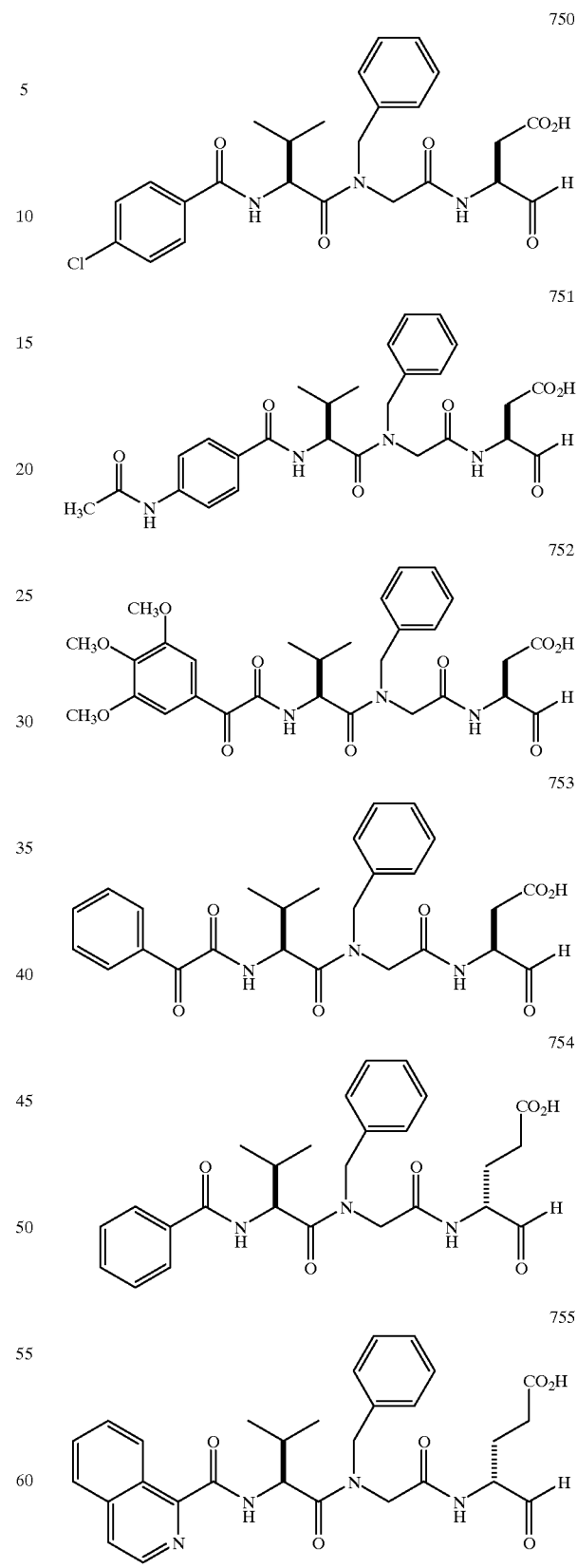

-continued

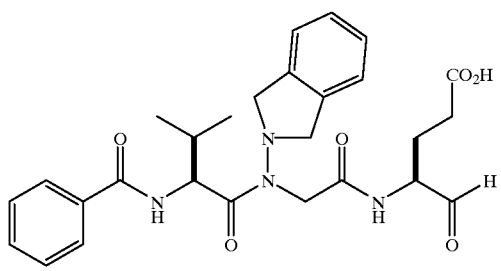

756

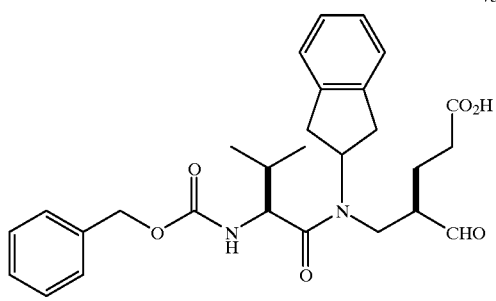

757

Other preferred compounds of this embodiment are those wherein:
$R_1$ is —C(O)—$R_8$;
$R_5$ is —C(O)—$R_7$ or —C(O)C(O)—$R_7$;

$R_4$ is a —$C_{1-5}$ straight or branched alkyl group optionally substituted by —Ar;

m is 1;

n is 1;

$R_3$ is —$CH_2$Ar, or

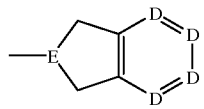

E is CH or N;

each D is independently N or C, wherein C is optionally substituted with —$OR_{14}$, —F, —Cl, —Br, —I, —$NO_2$, —$S(O)_2$—$N(R_9)$ $(R_{10})$, —C(O)—$N(R_9)$ $(R_{10})$, —N(H)—C(O)—$N(R_9)$ $(R_{10})$, —$N(R_9)$, —C(O)—$OR_9$, —$CF_3$, —$OCF_3$, a $C_{1-6}$ straight or branched alkyl group, 1,2—methylenedioxy, —CN, or —N(H)C($NR_9$) $N(R_9)$ $(R_{10})$;

each $R_9$ and $R_{10}$ is independently selected from the group consisting of —H, —Ar, and a —$C_{1-5}$ straight or branched alkyl group optionally substituted with —Ar.

Preferred compounds of this embodiment include but are not limited to:

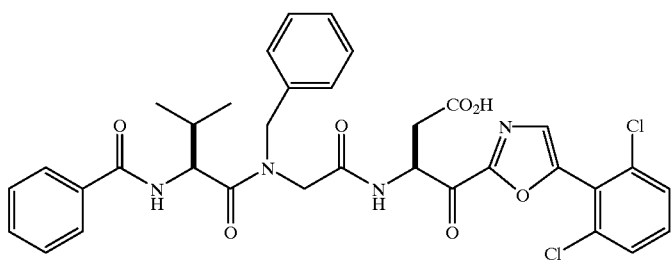

710

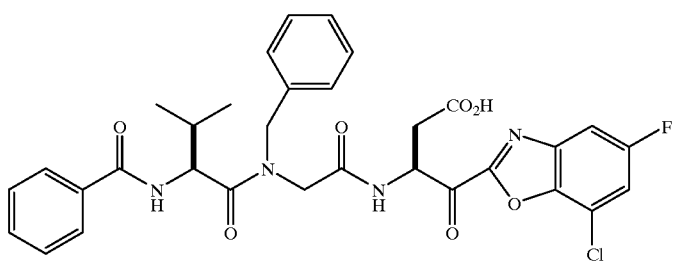

719

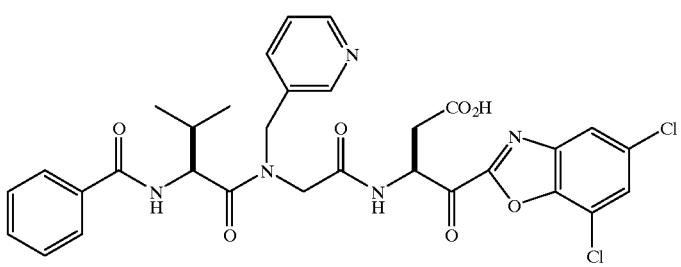

720

725
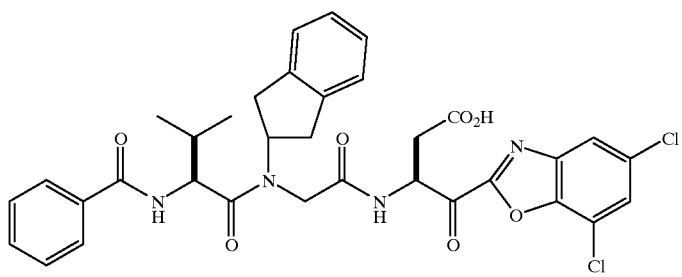
726
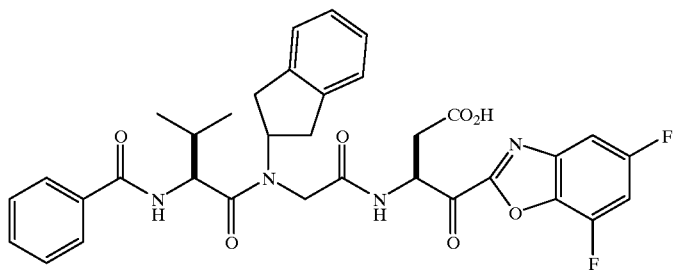
727
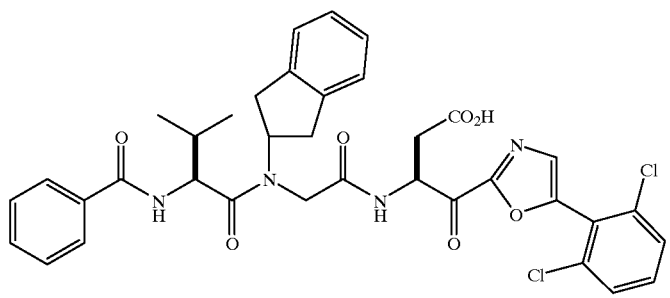
729
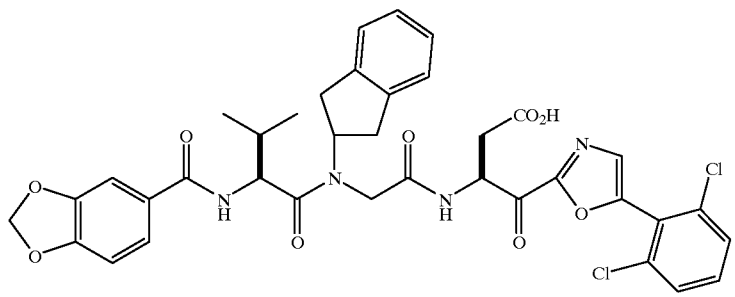
731
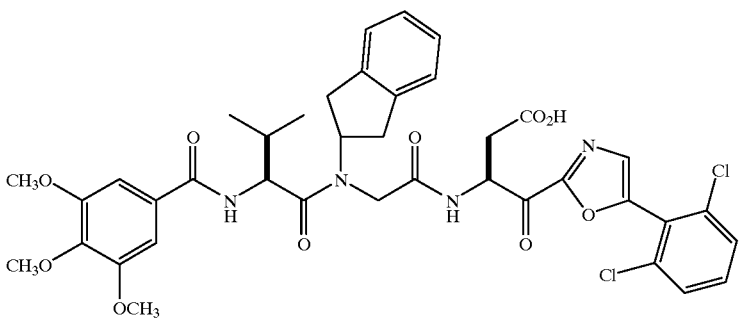

733

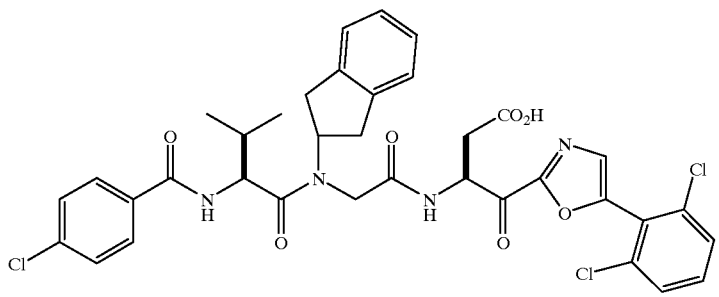

Other preferred compounds of this embodiment are those wherein $R_1$ is —C(O)—CH$_2$XR$_6$.

The ICE inhibitors of this invention may be synthesized using conventional techniques. Advantageously, these compounds are conveniently synthesized from readily available starting materials.

The compounds of this invention are among the most readily synthesized ICE inhibitors known. Previously described ICE inhibitors often contain four or more chiral centers and numerous peptide linkages. The relative ease with which the compounds of this invention can be synthesized represents an advantage in the large scale production of these compounds.

It should be understood that the compounds of this invention may exist in various equilibrium forms, depending on conditions including choice of solvent, pH, and others known to the practitioner skilled in the art. All such forms of these compounds are expressly included in the present invention. In particular, many of the compounds of this invention, especially those which contain aldehyde or ketone groups in $R_1$ and carboxylic acid groups ($R_2$=H), may take hemi-ketal (or hemi-acetal) or hydrated forms. For example, when $R_1$ is —(CO)—H and $R_2$ is —H compounds of this invention may take the forms depicted below:

Hydrated Form

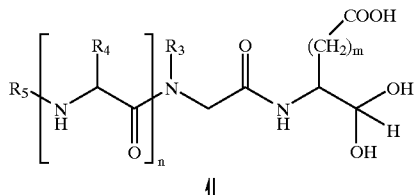

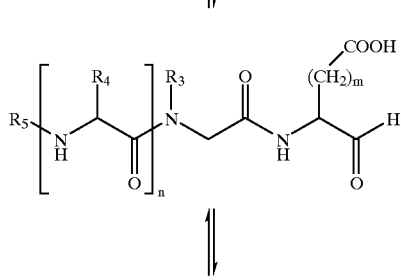

-continued
Hemi-ketal or
Hemi-acetal
Form

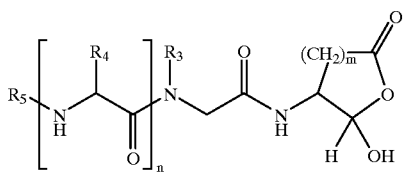

Depending on the choice of solvent and other conditions known to the practitioner skilled in the art, compounds of this invention may also take acyloxy ketal, acyloxy acetal, ketal or acetal form:

Acyloxy Ketal or
Acyloxy Acetal
Form

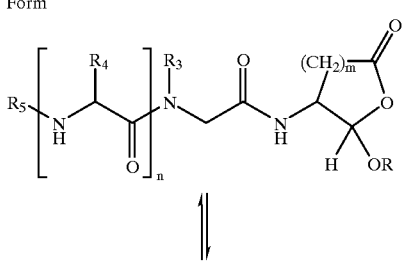

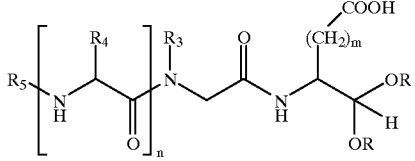

Ketal or
Acetal Form

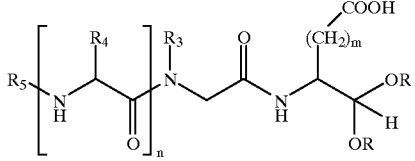

In addition, it should be understood that the equilibrium forms of the compounds of this invention may include tautomeric forms. All such forms of these compounds are expressly included in the present invention.

It should be understood that the compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. In addition, the compounds may be altered to pro-drug form such that the desired compound is created in the body of the patient as the result of the action of metabolic or other biochemical processes on the pro-drug. Such pro-drug forms typically demonstrate little or no activity in in vitro assays. Some examples of pro-drug forms include ketal, acetal, oxime, and hydrazone forms of compounds which contain ketone or aldehyde groups, especially where they occur in the $R_1$ group of the compounds of this invention. Other examples of pro-drug forms include the hemi-ketal, hemi-acetal, acylox, ketal, acyloxy acetal, ketal, and acetal forms that are described in EQ1 and EQ2.

The compounds of this invention are excellent ligands for ICE. Accordingly, these compounds are capable of targeting and inhibiting events in IL-1- and apoptosis-mediated diseases and, thus, the ultimate activity of that protein in inflammatory diseases, autoimmune diseases, proliferative disorders, infectious diseases, and degenerative diseases. For example, the compounds of this invention inhibit the conversion of precursor IL-1 β to mature IL-1 β by inhibiting ICE. Because ICE is essential for the production of mature IL-1, inhibition of that enzyme effectively blocks initiation of IL-1 mediated physiological effects and symptoms, such as inflammation, by inhibiting the production of mature IL-1. Thus, by inhibiting IL-1 β precursor activity, the compounds of this invention effectively function as IL-1 inhibitors.

The compounds of this invention may be employed in a conventional manner for the treatment of diseases which are mediated by IL-1 or apoptosis. Such methods of treatment, their dosage levels and requirements may be selected by those of ordinary skill in the art from available methods and techniques. For example, a compound of this invention may be combined with a pharmaceutically acceptable adjuvant for administration to a patient suffering from an IL-1- or apoptosis-mediated disease in a pharmaceutically acceptable manner and in an amount effective to lessen the severity of that disease.

Alternatively, the compounds of this invention may be used in compositions and methods for treating or protecting individuals against IL-1- or apoptosis-mediated diseases over extended periods of time. The compounds may be employed in such compositions either alone or together with other compounds of this invention in a manner consistent with the conventional utilization of ICE inhibitors in pharmaceutical compositions. For example, a compound of this invention may be combined with pharmaceutically acceptable adjuvants conventionally employed in vaccines and administered in prophylactically effective amounts to protect individuals over an extended period time against IL-1- or apoptosis-mediated diseases.

The compounds of this invention may also be co-administered with other ICE inhibitors to increase the effect of therapy or prophylaxis against various IL-1- or apoptosis-mediated diseases.

In addition, the compounds of this invention may be used in combination either conventional anti-inflammatory agents or witty matrix metalloprotease inhibitors, lipoxygenase inhibitors and antagonists of cytokines other than IL-1 β.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexone and rEPO) or with prostaglandins, to prevent or combat IL-1- or apoptosis-mediated disease symptoms such as inflammation.

When the compounds of this invention are administered in combination therapies with other agents, they may be administered sequentially or concurrently to the patient. Alternatively, pharmaceutical or prophylactic compositions according to this invention may be comprised of a combination of an ICE inhibitor of this invention and another therapeutic or prophylactic agent.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally or via an implanted reservoir. We prefer oral administration. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in *Ph. Helv.* (Pharmacopeia Helvetica) or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 1 and 50 mg/kg body weight per day of the active ingredient compound are useful in the prevention and treatment of IL-1- and apoptosis-mediated diseases, including inflammatory diseases, autoimmune diseases, destructive bone disorders, proliferative disorders, infectious diseases, degenerative diseases, osteoarthritis, pancreatitis, asthma, adult respiratory distress syndrome, glomeralonephritis, rheumatoid arthritis, systemic lupu, erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, graft vs. host disease, osteoporosis, multiple myeloma-related bone disorder, acute myelogenous leukemia, chronic myelogenous leukemia, metastatic melanoma, Kaposi's sarcoma, multiple myeloma sepsis, septic shock, Shigellosis, Alzheimer's disease, Parkinson's disease, cerebral ischemia, myocardial ischemia, spinal muscular atrophy, multiple sclerosis, AIDS-related encephalitis, HIV-related encephalitis, and neurological damage due to stroke. Typically, the pharmaceutical compositions of this invention will be administered from about 1 to 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency o administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

The IL-1 or apoptosis-mediated diseases which may be treated or prevented by the compounds of this invention include, but are not limited to, inflammatory diseases, autoimmune diseases, proliferative disorders, infectious diseases, degenerative, and necrotic diseases.

Inflammatory diseases which may be treated or prevented include, but are not limited to osteoarthritis, acute pancreatitis, chronic pancreatitis, asthma, and adult respiratory distress syndrome. Preferably, the inflammatory disease is osteoarthritis or acute pancreatitis.

Autoimmune diseases which may be treated or prevented include, but are not limited to, glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, and graft vs. host disease. Preferably, the autoimmune disease is rheumatoid arthritis, inflammatory bowel disease, Crohn's disease, or psoriasis.

Bone destructive disorders which may be treated or prevented include, but are not limited to, osteoporosis and multiple myeloma-related bone disorder.

Proliferative diseases which may be treated or prevented include, but are not limited to, acute myelogenous leukemia, chronic myelogenous leukemia, metastatic melanoma, Kaposi's sarcoma, and multiple myeloma.

Infectious diseases which may be treated or prevented include, but are not limited to, sepsis, septic shock, and Shigellosis.

The IL-1-mediated degenerative or necrotic diseases which may be treated or prevented by the compounds of this invention include, but are not limited to, Alzheimer's disease, Parkinson's disease, cerebral ischemia, and myocardial ischemia. Preferably, the degenerative disease is Alzheimer's disease.

The apoptosis-mediated degenerative diseases which may be treated or prevented by the compounds of this invention include, but are not limited to, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

Although this invention focuses on the use of the compounds disclosed herein for preventing and treating IL-1 and apoptosis-mediated diseases, the compounds of this invention can also be used as inhibitory agents for other cysteine proteases.

The compounds of this invention are also useful as commercial reagents which effectively bind to ICE or other cysteine proteases. As commercial reagents, the compounds of this invention, and their derivatives, may be used to block proteolysis of a target peptide in biochemical or cellular assays for ICE and ICE homologs or may be derivatized to bind to a stable resin as a tethered substrate for affinity chromatography applications. These and other uses which characterize commercial cysteine protease inhibitors will be evident to those of ordinary skill in the art.

In order that this invention be more fully understood, the following examples are set forth. These examples are for the purpose of illustration only and are not to be construed as limiting the scope of the invention in any way.

EXAMPLE 1

Inhibition of ICE

We obtained inhibition constants ($K_i$) and $IC_{50}$ values for several compounds of this invention using the three methods described below:

1. Enzyme assay with UV-visible substrate

This assay is run using an Succinyl-Tyr-Val-Ala-Asp-pNitroanilide substrate. Synthesis of analogous substrates is described by L. A. Reiter (Int. J. Peptide Protein Res. 43, 87–96 (1994)). The assay mixture contains:

65 µl buffer (10 mM Tris, 1 mM DTT, 0.1% CHAPS @ pH 8.1)

10 µl ICE (50 nM final concentration to give a rate of ~1 mOD/min)

5 µl DMSO/Inhibitor mixture

20 µl 400 µM Substrate (80 µM final concentration)

100 µl total reaction volume

The visible ICE assay is run in a 96-well microtiter plate. Buffer, ICE and DMSO (if inhibitor is present) are added to the wells in the order listed. The components are left to incubate at room temperature for 15 minutes starting at the time that all components are present in all wells. The microtiter plate reader is set to incubate at 37° C. After the 15 minute incubation, substrate is added directly to the wells and the reaction is monitored by following the release of the chromophore (pNA) at 405–603 nm at 37° C. for 20 minutes. A linear fit of the data is performed and the rate is calculated in mOD/min. DMSO is only present during experiments involving inhibitors, buffer is used to make up the volume to 100 µl in the other experiments.

EXAMPLE 2

The following $K_i$ values were determined for compounds 706, 710, 719, 720, 725–727, 729, 731, 733, 743, 745, and 747–757 using the assay described in Example 1. The structures of the compounds of Example 2 are shown in the following Table and in Example 3.

| Cpd | Type | A | B | C | D | $K_i$ (nM) |
|---|---|---|---|---|---|---|
| 706 | 1 | H | CH₂-phenyl | i-Pr | phenyl | 69 |
| 710 | 1 | 2-methyl-oxazole-5-(2,6-dichlorophenyl) | CH₂-phenyl | i-Pr | phenyl | 20 |

-continued

Type 1: D-NH-C(C)(H)-C(=O)-N(B)-CH2-C(=O)-NH-CH(CO2H)-C(=O)-A

Type 2: D-NH-C(C)(H)-C(=O)-N(B)-CH2-C(=O)-NH-CH(CH2CH2CO2H)-C(=O)-A

| Cpd | Type | A | B | C | D | $K_i$ (nM) |
|---|---|---|---|---|---|---|
| 719 | 1 | 2-methyl-5-fluoro-7-chloro-benzoxazole | benzyl (CH2-phenyl) | i-Pr | phenyl | 20 |
| 720 | 1 | 2-methyl-5,7-dichloro-benzoxazole | 3-pyridylmethyl | i-Pr | phenyl | 33 |
| 725 | 1 | 2-methyl-5,7-dichloro-benzoxazole | 2-indanyl | i-Pr | phenyl | 1.9 |
| 726 | 1 | 2-methyl-5,7-difluoro-benzoxazole | 2-indanyl | i-Pr | phenyl | 15 |
| 727 | 1 | 2-methyl-5-(2,6-dichlorophenyl)oxazole | 2-indanyl | i-Pr | phenyl | 9.0 |
| 729 | 1 | 2-methyl-5-(2,6-dichlorophenyl)oxazole | 2-indanyl | i-Pr | 3,4-methylenedioxyphenyl | 4.7 |
| 731 | 1 | 2-methyl-5-(2,6-dichlorophenyl)oxazole | 2-indanyl | i-Pr | 3,4,5-trimethoxyphenyl | 26 |

-continued

Type 1 / Type 2 structures (peptide scaffolds with substituents A, B, C, D)

| Cpd | Type | A | B | C | D | K_i (nM) |
|---|---|---|---|---|---|---|
| 733 | 1 | 2-methyl-5-(2,6-dichlorophenyl)oxazole | 2-indanyl (CH) | i-Pr | 4-chlorophenyl | 7.5 |
| 737 | 1 | H | 3-aminomethylaniline (H₂C—C₆H₄—NH₂) | i-Pr | phenyl | |
| 739 | 1 | H | 3-(guanidino)benzyl | i-Pr | phenyl | |
| 741 | 1 | H | 3-(ureido)benzyl | i-Pr | phenyl | |
| 743 | 1 | H | 3-(acetylamino)benzyl | i-Pr | phenyl | 60 |
| 745 | 1 | H | 3-(methanesulfonylamino)benzyl | i-Pr | phenyl | 45 |
| 746 | 1 | H | benzyl (CH₂) | t-Bu | phenyl | |
| 747 | 1 | H | benzyl (CH₂) | t-Bu | 1-methylisoquinolinyl | 24 |
| 748 | 1 | H | benzyl (CH₂) | i-Pr | 1-methylisoquinolinyl | 6 |

-continued

Type 1: structure with CO2H group (aspartate-based)
Type 2: structure with CO2H group (glutamate-based)

| Cpd | Type | A | B | C | D | K_i (nM) |
|---|---|---|---|---|---|---|
| 749 | 1 | H | PhCH2 | i-Pr | 1-methylnaphthalene | 7 |
| 750 | 1 | H | PhCH2 | i-Pr | 4-chlorobenzyl | 90 |
| 751 | 1 | H | PhCH2 | i-Pr | 4-(acetylamino)benzyl | 71 |
| 752 | 1 | H | PhCH2 | i-Pr | 3,4,5-trimethoxyphenacyl | 62 |
| 753 | 1 | H | PhCH2 | i-Pr | phenacyl | 53 |
| 754 | 2 | H | PhCH2 | i-Pr | phenyl | 2500 |
| 755 | 2 | H | PhCH2 | i-Pr | 1-methylisoquinoline | 390 |
| 756 | 1 | H | N-methylisoindoline | i-Pr | phenyl | |

-continued

| | | | | | | |
|---|---|---|---|---|---|---|
| Cpd | Type | A | B | C | D | $K_i$ (nM) |
| 757 | 1 | H | 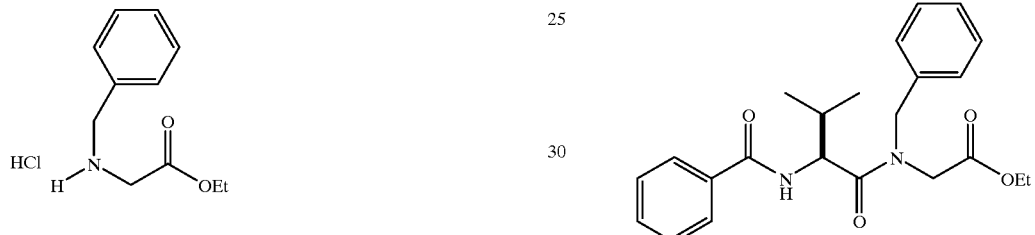 | i-Pr | | 170 |

Type 1 and Type 2 structures shown above.

EXAMPLE 3
Compounds of Example 2 were synthesized as follows:

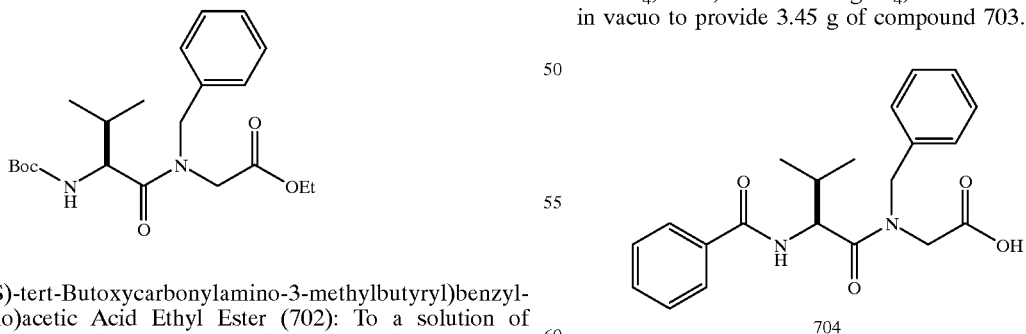

N-Benzylglycine Ethyl Ester (701): To a solution of benzaldehyde (14.0 g, 0.132 mol) in absolute EtOH (500 mL) was added glycine ethyl ester hydrochloride (37.0 g, 0.256 mol), NaoAc (32.5 g, 0.396 mol) and sodium cyanoborohydride (9.8 g, 0.158 mol), and the resulting mixture heated to reflux. After 1 hr at reflux, the reaction was cooled and concentrated in vacuo. The residue was taken up into 1N NaOH and EtOAc. The layers were separated and the organic phase was washed with 1N NaOH, brine, dried over $MgSO_4$, filtered and concentrated in vacuo. The residue was taken up into EtOAc (150 mL) and treated with gaseous HCl. The resulting solid was collected, washed with $Et_2O$ and dried to provide 23.4 g of compound 701 as the HCl salt.

((2(S)-tert-Butoxycarbonylamino-3-methylbutyryl)benzyl-amino)acetic Acid Ethyl Ester (702): To a solution of N-Boc-valine (2.18 g, 10 mmol) and DIEA (4.4 mL, 25.3 mmol) in $CH_2Cl_2$ (20 mL) at −20° C. was added trimethylacetyl chloride (1.2 mL, 9.7 mmol). After stirring for 30 min, compound 701 (2.18 g, 10 mmol) was added and the reaction allowed to warm to rt and stir for 5 hr. The reaction was concentrated in vacuo and the residue taken up into EtOAc. and $H_2O$. The layers were separated and the organic phase washed with sat. aq. $NaHCO_3$, sat. aq. $KHSO_4$, brine, dried over $MgSO_4$, filtered and concentrated in vacuo to provide 3.45 g of compound 702.

((2(S)-Benzoylamino-3-methylbutyryl)benzylamino)acetic Acid Ethyl Ester (703): To a solution of compound 702 (3.45 g, 8.8 mmol) in EtOAc at 0° C. was bubbled in gaseous HCl until saturated. The reaction was warmed to rt and stirred for 3 hr. Nitrogen was bubbled through the reaction to remove excess HCl, followed by concentration in vacuo. The residue suspended in $CH_2Cl_2$ (50 mL), treated with DIEA (3.4 mL, 19.5 mmol) followed by benzoyl chloride (1.2 mL, 10.3 mmol) and the reaction allowed to stir overnight. The reaction was concentrated in vacuo and the residue taken up into EtOAc and $H_2O$. The layers were separated and the organic phase washed with sat. aq. $NaHCO_3$, sat. aq. $KHSO_4$, brine, dried over $MgSO_4$, filtered and concentrated in vacuo to provide 3.45 g of compound 703.

((2(S)-Benzoylamino-3-methylbutyryl)benzylamino)acetic Acid (704): To a solution of compound 703 (3.45 g, 8.8 mmol) in MeOH (9 mL) was added 1N LiOH (9 mL) and the reaction allowed to stir over night. The reaction was concentrated in vacuo and the residue taken up into EtOAc and $H_2O$. The layers were separated and the aqueous phase was acidified with 1N HCl. The product was extracted with EtOAc (2×). The extracts were combined, washed with brine, dried over MgSO₄, filtered and concentrated in vacuo to provide 3.0 g of compound 704.

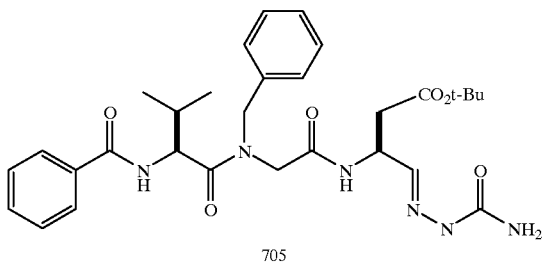

3(S)-(2-((2(S)-Benzoylamino-3-methylbutyryl)benzyl-amino)acetylamino)-4-oxo-butyric Acid tert-Butyl Ester Semicarbazone (705): To a solution of 3(S)-(1-fluorenylmethyloxycarbonylamino)-4-oxobutyric acid tert-butyl ester semicarbazone (678 mg, 1.5 mmol; Prepared in a similar manner to the benzyloxycarbonyl analog in Graybill et al., *Int. J. Protein Res.*, 44, pp. 173–82 (1994)) in acetonitrile (5.0 mL) was added diethylamine (780 μL, 7.5 mmol) and the reaction allowed to stir at rt for 1 hr. The reaction was concentrated in vacuo and the residue co-concentrated with toluene (3×) in vacuo. To a suspension of the residue, compound 704 (555 mg, 1.5 mmol) and HOBT (224 mg, 1.66 mmol) in 1:1 CH₂Cl.DMF (10 mL) at 0° C., was added EDC (318 mg, 1.66 mmol). The reaction was warmed to rt and stirred over night. The reaction was diluted with EtOAc and H₂O. The layers were separated and the organic phase washed with sat. aq. NaHCO₃, sat. aq. KHSO₄, brine, dried over MgSO₄, filtered and concentrated in vacuo. Chromatography of the residue on silica gel (elution with 2–6% MeOH:CH₂Cl₂) provided 600 mg of compound 705.

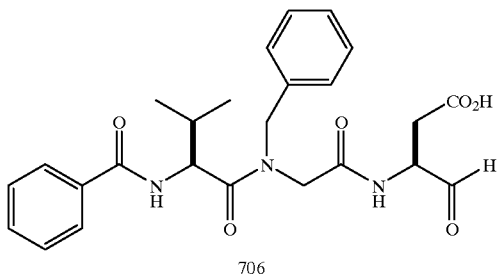

3(S)—(2-((2(S)-Benzoylamino-3-methylbutyryl)benzylamino)acetylamino)-4-oxo-butyric Acid (706): To a suspension of compound 705 (600 mg, 1.04 mmol) in CH₂Cl₂(10 mL) was added TFA (4.0 mL) and the reaction allowed to stir for 4 hr. The reaction was concentrated in vacuo and the residue co-concentrated with toluene (3×). The residue was dissolved in MeOH (10 mL) and treated with HOAc (2.0 mL) followed by formaldehyde (2.0 mL). After stirring for 3 hr at rt, the reaction was concentrated in vacuo. Prep-HPLC provided 89 mg of compound 706: ¹H NMR (500 MHz, CD₃OD) δ 8.34–8.21 (m), 7.80–7.69 (m), 7.51–7.02 (m), 4.99–4.81 (m), 4.73–4.59 (m), 4.57–4.56 (m), 4.35– 4.12 (m), 4.07–3.96 (m), 3.93–3.84 (m), 2.64–2.51 (m), 2.49–2.31 (m), 2.29–2.13 (m), 1.02–0.80 (m).

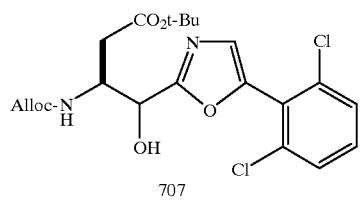

3(S)-(Allyloxycarbonyl)-amino-4-((2,6-dichloro-phenyl)-5-cxazol-2-yl)-4-hydroxy-butyric Acid tert-Butyl Ester (707). A solution of 5-(2,6-Dichloro-phenyl)oxazole (2.71 g, 12.7 mmol; prepared by a similar method described in *Tet. Lett.* 2369 (1972)) in THF (65 mL) was cooled to −78° C. under a nitrogen atmosphere. To this solution was added n- butyl lithium (1.5M solution in hexane, 8.5 mL, 13.3 mmol). After 30 min. Magnesium bromide etherate (3.6 g, 13.9 mmol) was added and the solution was allowed to warm to −45° C. for 15 min. The reaction was cooled to −78° C. and 3(S)-(1-allyloxycarbonylamino)-4-oxobutyric acid tert-butyl ester (3.26 g, 12.7 mmol; Graybill et al., *Int. J. Protein Res.*, 44, 173–182 (1993)) in THF (65 mL) was added dropwise. The reaction was stirred for 25 min., then allowed to warm to −40° C. and stirred for 3 h, and then at rt for 1 h. The reaction was quenched with 5% NaHCO₃ (12 mL) and stirred for 3 h. The THF was removed in vacuo and the resulting residue was extracted with CH₂Cl₂. The organic layer was washed with brine and dried over MgSO₄, filtered, and concentrated in vacuo to yield 6.14 g. Purification gave 4.79 g of compound 707.

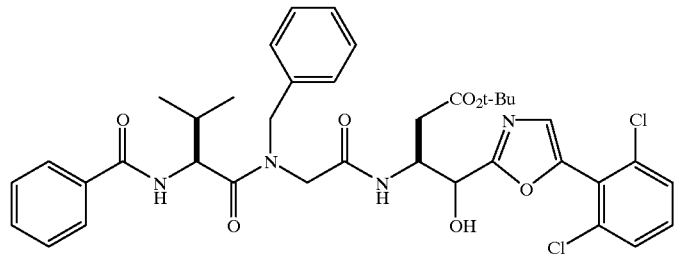

3(S)-(2-((2(S)-Benzoylamino-3-methylbutyryl)benzyl-amino)acetylamino)-4-(4-(2,6-dichlorophenyl)-oxazol-2-yl)-4-hydroxybutyric Acid tert-Butyl Ester (708): To a suspension of compound 704 (318 mg, 0.86 mmol) and compound 707 (370 mg, 0.78 mmol) in 1:1 $CH_2Cl_2$:DMF (8.0 mL) was added bis(triphenylphosphine) palladium dichloride (10 mg), followed by the dropwise addition of tri-n-butyl tin hydride (320 μL, 1.19 mmol). After the addition was complete, HOBT (212 mg, 1.57 mmol) was added and the reaction was cooled to 0° C. added EDC (180 mg, 0.94 mmol) was added and the reaction allowed to warm to rt and stir overnight. The reaction was concentrated in vacuo and the residue taken up into EtOAc and sat. aq. $KHSO_4$. The layers were separated and the organic phase was washed with sat. aq. $K_2CO_3$, brine, dried over $MgSO_4$, filtered and concentrated in vacuo. Chromatography on silica gel (elution with 2% MeOH:$CH_2Cl_2$) provided 150 mg of compound 708.

3(S)-(2-((2(S)-Benzoylamino-3-methylbutyryl)benzylamino)acetylamino)-4-(4-(2,6-dichlorophenyl)-oxazol-2-yl)-4-oxobutyric Acid (710): To a solution of compound 709 in $CH_2Cl_2$ (4.0 mL) was added TFA (2.0 mL) and the reaction stirred at rt for 1 hr. The reaction was concentrated in vacuo and the residue co-concentrated with toluene. Prep- HPLC provided 35 mg of compound 710: $^1$H NMR (500 MHz, $CD_3OD$) δ 8.90 (m), 8.52 (m), 8.35 (m), 7.83 (m), 7.62–7.39 (m), 7.38–7.16 (m), 5.52 (m), 5.01 (m), 5.01 (m), 4.99–4.53 (m), 4.42 (m), 4.33–3.82 (m), 3.16–2.93 (m), 2.91–2.48 (m), 2.24 (m), 1.09–0.85 (m).

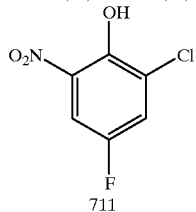

711

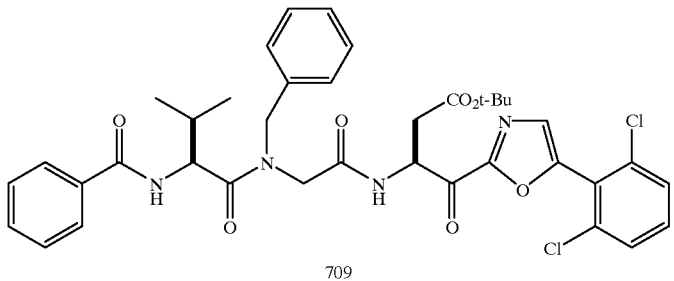

709

3(S)-(2- ((2(S) -Benzoylamino-3-methylbutyryl) benzylamino)acetylamino)-4-(4-(2,6-dichlorophenyl)-oxazol-2-yl)-4-oxobutyric Acid tert-Butyl Ester (709): To a suspension of Dessmarten (259 mg, 0.61 mmol) in $CH_2Cl_2$ (4.0 mL) was added dropwise a solution of compound 708 (150 mg, 0.20 mmol) in $CH_2Cl_2$ (2.0 mL). After stirring at rt for 1 hr. the reaction was concentrated in vacuo. The residue was dissolved into EtOAc and washed with 1:1 sat. aq. $Na_2S_2O_3$:sat. aq. $NaHCO_3$, sat. aq. $NaHCO_3$, brine, dried over $MgSO_4$, filtered and concentrated in vacuo. Chromatography on silica gel (elution with 2–5% MeOH: $CH_2Cl_2$) provided 74 mg of compound 709.

2-Chloro-4-fluoro-6-nitrophenol (711): To a mixture of 2-Chloro-4-fluorophenol (25 g, 0.171 mol) in $H_2O$ (100 mL) and $Et_2O$ (300 mL) at 0° C. was added dropwise concentrated nitric acid (25 mL). After the addition was complete the reaction was warmed to rt and stirred for 3 hr. The layers were separated and the organic phase washed with 1:1 brine:$H_2O$, brine, dried over $MgSO_4$, filtered and concentrated in vacuo to a slurry.

The slurry was diluted with hexane and the yellow solid collected and dried to provide 23.6 g of compound 711.

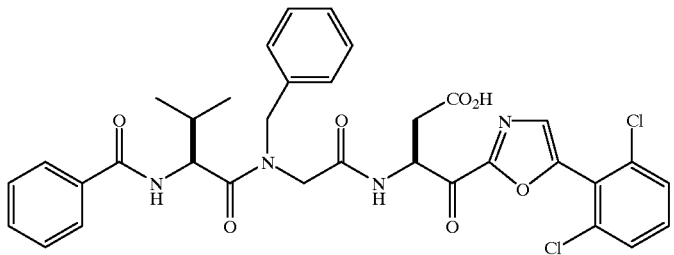

710

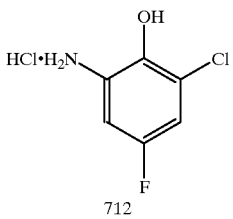

712

2-Chloro-4-fluoro-6-aminophenol Hydrochloride (712): A mixture of compound 711 (23.4 g, 0.122 mol) and platinum oxide (2.3 g) in absolute EtOH (120 mL) was placed under 1 atm of hydrogen and stirred until complete reduction had occurred. The hydrogen was replaced with nitrogen and the reaction was filtered through Celite. The filtrate was diluted with Et$_2$O (300 mL) and gaseous hydrochloric acid was bubbled through the solution to provide a white precipitate. The solid was collected and dried under vacuum to provide 17.1 g of compound 712 as a white solid.

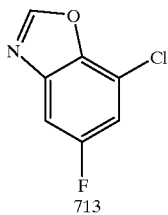

713

6-Chloro-4-fluorobenzoxazole (713): A mixture of compound 712 (17.0 g, 86.3 mmol) and trimethylorthoformate (18.9 mL, 0.173 mol) in absolute MeOH (90 mL) was heated to reflux upon which a solution formed. After stirring at reflux for 24 hr, the reaction was cooled and concentrated to provide an orange solid. The solid was dissolved into Et$_2$O, washed with 1N NaOH, brine, dried over MgSO$_4$, filtered and concentrated to provide a yellow orange solid. Recyrstallization from hot aqueous EtOH with rapid cooling and filtration provided 10.0 g of compound 713 as white needles. Note that prolong standing in aqueous EtOH causes decomposition of compound 713.

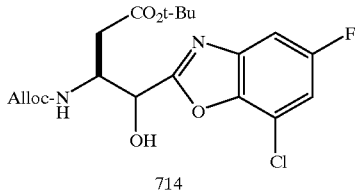

714

3(S)-(Allyloxycarbonyl)-amino-4-(6-chloro-4-fluorobenzoxazol-2-yl)-4-hydroxy-butyric Acid tert-Butyl Ester (714). To a solution compound 713 (2.06 g, 12.0 mmol) in THF (24 mL) at −78° C. was added dropwise butyl lithium (1.6 M in hexane, 7.0 mL, 12.1 mmol) and the reaction allowed to stir for 1 hr. The reaction was treated with solution of magnesium bromide (1M in benzene:Et$_2$O 1:4, 13.2 mL) and the reaction warmed to −40° C. After stirring for 1 hr, the reaction was cooled to −78° C. and treated with a solution of 3(S)-(1-allyloxycarbonylamino)-4-oxobutyric acid tert-butyl ester (2.57 g, 10 mmol) in THF (12 mL). The reaction was allowed to slowly warm to rt and stir overnight. The reaction was quenched with sat. aq. NH$_4$Cl, diluted with EtOAc and enough H$_2$O added to make the aqueous phase clear. The layers were separated and the organic phase washed with brine, dried over MgSO$_4$, filtered and concentrated in vacuo. Chromatography of the residue on silica gel (elution with 15–45% EtOAc:hexane) provided 2.0 g of compound 714.

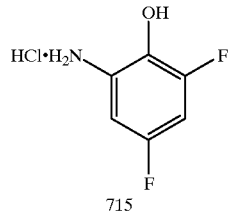

715

2,4-Difluoro-6-aminophenol Hydrochloride (715): A mixture of 2,4-Difluoro-6-nitrophenol (28.4 g, 0.162 mol; prepared by a similar method as 711 except replacing 2-chloro-4-fluorophenol with 2,4-difluorophenol) and 10% palladium on carbon (3.5 g) in absolute MeOH (120 mL) was placed under 1 atm of H$_2$ and stirred until complete reduction had occurred. The H$_2$ was replaced with nitrogen and the reaction was filtered through Celite. Gaseous HCl was bubbled through the filtrate and the resulting solution concentrated. The residue was taken up into H$_2$O, washed with Et$_2$O (2×), neutralized with solid NaHCO$_3$ and the product extracted with Et$_2$O. The extracts were combined dried over MgSO$_4$ and filtered. The filtrate was treated with gaseous HCl and resulting precipitate collected and dried under vacuum to provide 12.9 g of compound 715 as a beige solid.

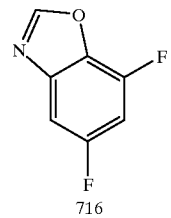

716

4,6-Difluorobenzoxazole (716): A mixture of compound 715 (12.8 g, 70.7 mmol) and trimethylorthoformate (23 mL, 0.212 mol) in absolute MeOH (90 mL) was heated to reflux upon which a solution formed. After stirring at reflux for 24 hr, the reaction was cooled and concentrated. The residue was dissolved into Et$_2$O, washed with 1N sodium hydroxide, brine, dried over MgSO$_4$, filtered and concentrated. Distillation under reduced pressure afforded 5.0 g of compound 716 as a clear liquid, which solidified upon standing.

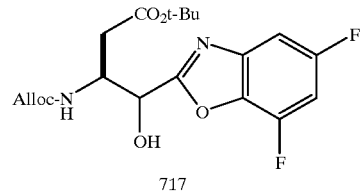

717

3(S)-(Allyloxycarbonyl)-amino-4-(4,6-difluorobenzoxazol-2-yl)-4-hydroxy-butyric Acid tert-Butyl Ester (717). compound 717 was prepared as described for compound 714, except compound 713 was replaced with compound 716.

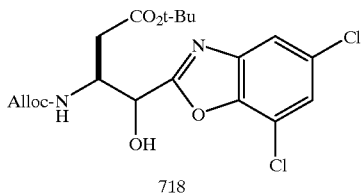

3(S)-(Allyloxycarbonyl)-amino-4-(4,6-dichorobenzoxazol-2-yl)-4-hydroxy-butyric Acid tert-Butyl Ester (718). compound 718 was prepared by a similar method as that used for compound 714, except compound 711 was replaced with 2,4-dichloro-6-nitrophenol.

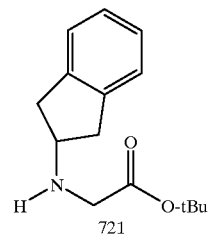

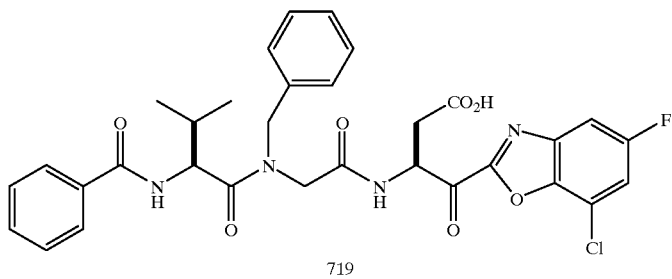

3(S)-(2- ((2(S) -Benzoylamino-3-methylbutyryl)benzyl-amino)acetylamino)-4-(6-chloro-4-fluorobenzoxazol-2-yl)-4-oxobutyric Acid (719): Compound 719 was prepared by a method similar to the method used to prepare compound 710, except compound 707 was replaced with compound 714 in the preparation of 708: $^1$H NMR (500 MHz, CD$_3$OD) 67 8.70–8.54 (m), 8.48–8.35 (m), 8.34–8.08 (m), 7.98–7.87 (m), 7.75–7.67 (m), 7.63 (m), 7.58 (m), 7.51–7.44 (m), 7.43–7.29 (m), 7.28–7.03 (m), 6.97 (m), 5.51 (m), 4.99–4.66 (m), 4.65–4.26 (m), 4.25–3.61 (m), 3.42 (m), 3.13–2.83 (m), 2.68–2.42 (m), 2.23–2.00 (m), 1.02–0.69 (m).

N-Indan-2-ylglycine t-Butyl Ester (721): To a suspension of 2-aminoindane hydrochloride (5.0 g, 29.5 mmol) and powdered K$_2$CO$_3$ (8.3 g, 60.0 mmol) in absolute EtOH (30 mL) was added tert-butyl bromoacetate (4.4 mL, 29.5 mmol). After stirring for 10 min at rt the reaction was heated to 45° C. and stirred for 2 hr. The reaction was cooled to rt, diluted with EtOAc, filtered and concentrated. Chromatography of the residue on silica gel (elution with 20% EtOAc:hexane) provided 4.7 g of compound 721 as a white crystalline solid.

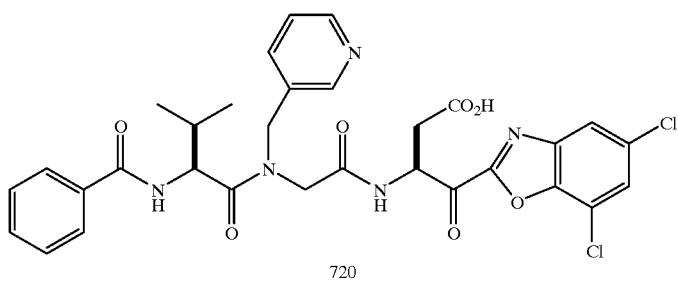

3(S)-(2-((2(S)-Benzoylamino-3-methylbutyryl)-3-picolylamino)acetyl-amino)-4-(4,6-dichlorobenzoxazol-2-yl)-4-oxobutyric Acid (720): Compound 720 was prepared by a method similar to the method used to prepare compound 710, except replacing benzaldehyde with 3-pyridinecarboxaldehyde in the preparation of 701 and replacing compound 707 with compound 718 in the preparation of 708: $^1$H NMR (500 MHz, CD$_3$OD) δ 8.88–8.44 (m), 8.42–8.20 (m), 7.91–7.58 (m), 7.55–7.30 (m), 5.51 (m), 4.72–4.11 (m), 3.92–3.52 (m), 3.26–2.92 (m), 2.72–2.51 (m), 2.32–1.91 (m), 1.46–1.21 (m), 1.11–0.68 (m).

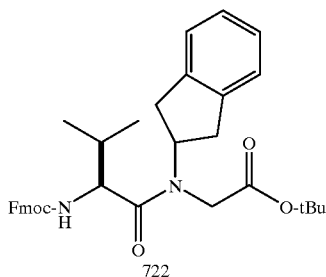

722

((2(S)-Fluorenylmethyloxycarbonylamino-3-methylbutyryl) indan-2-ylamino)acetic Acid t-Butyl Ester (722): To a partial solution of N-Fmoc-valine (9.08 g, 26.8 mmol) in $CH_2Cl_2$ (50 mL) containing DMF (100 μ) was slowly added oxalyl chloride (3.5 mL, 40.2 mmol) upon which an evolution of gas occurred and a yellow solution formed. After stirring for 30 min, the reaction was concentrated in vacuo. The residue was dissolved in $CH_2Cl_2$ (25 mL) and treated with DIEA (2.3 mL, 13.4 mmol) followed by a solution of compound 721 (3.31 g, 13.4 mmol) in $CH_2Cl_2$. After stirring overnight, the reaction was diluted with EtOAc, washed with 5% $NaHCO_3$, brine, dried over $MgSO_4$, filtered and concentrated in vacuo. Chromatography of the residue on silica gel (elution with 10–20% EtOAc:hexane) provided 7.2 g of compound 722.

723

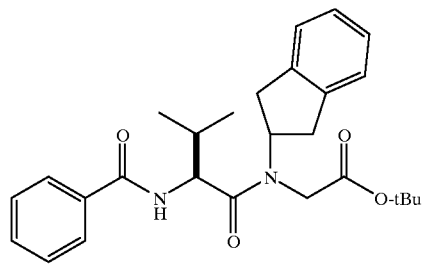

((2(S)-Benzoylamino-3-methylbutyryl)indan-2-ylamino) acetic Acid t-Butyl Ester (723): To a solution of compound 722 (500 mg, 0.88 mmol) in $CH_3CN$ (6.0 mL) was added diethylamine (455 μ, 4.4 mmol) and the reaction allowed to stir for 2 hr. The reaction was concentrated and the residue co-concentrated with toluene (2×) to provide a viscous oil. The residue was dissolved in $CH_2Cl_2$ (5 mL) containing DMF (2 mL), treated with benzoic acid (161 mg, 1.32 mmol) followed by EDC (252 mg, 1.32 mmol) and the reaction allowed to stir overnight. The reaction was diluted with EtOAc and washed with $H_2O$. The aqueous layer was re-extracted with EtOAc. The extracts were combined washed with 5% $KHSO_4$, filtered and concentrated in vacuo. Chromatography of the residue on silica gel (elution with 10% EtOAc:hexane) provided 240 mg of compound 723.

724

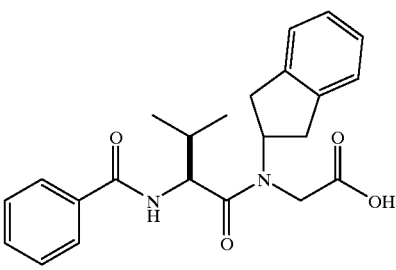

((2(S)-Benzoylamino-3-methylbutyryl)indan-2-ylamino) acetic Acid (24): To a solution of compound 723 (240 mg, 0.53 mmol) in $CH_2Cl_2$ (4.0 mL) was added TFA (2.0 mL) and the reaction stirred at rt for 1 hr. The reaction was concentrated in vacuo and the residue co-concentrated with toluene. The material was used directly in the next reaction without further purification.

725

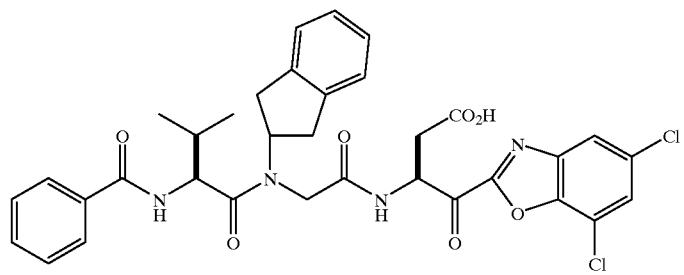

3(S)-(2-((2(S)-Benzoylamino-3-methylbutyryl)indan-2-ylamino)acetylamino)-4-(4,6-dichlorobenzoxazol-2-yl)-4-oxobutyric Acid (725): Compound 725 was prepared by a method similar to the method used to prepare compound 710, except compound 704 was replaced with compound 724 is and compound 707 was replaced with compound 718 in the preparation of compound 708: $^1$H NMR (500 MHz, CD$_3$OD) δ 8.7–8.6 (m), 8.6–8.4 (m), 8.1 (d), 8.0–7.8 (m), 7.6–7.5 (m), 7.5–7.4 (m), 7.2–7.0 (m), 7.0–6.9 (m), 5.5–5.3 (m), 5.3–5.2 (m), 4.6–4.5 (m), 4.5–4.3 (m), 4.2–4.0 (m), 3.8–3.6 (m), 3.3 (s), 3.2–3.1 (m), 3.1–3.0 (m), 3.0–2.8 (m), 2.7–2.6 (m), 2.4–2.0 (m), 1.2–0.6 (m).

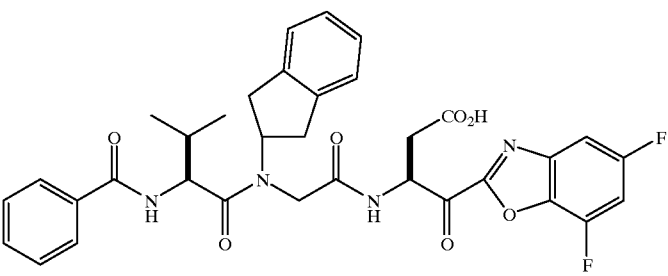

726

3(S)-(2-(2(S)-Benzoylamino-3-methylbutyryl)indan-2-ylamino)acetylamino)-4-(4,6-difluorobenzoxazol-2-yl)-4-oxobutyric Acid (726): Compound 726 was prepared by a method similar to the method used to prepare compound 710, except compound 704 is replaced with compound 724 and compound 707 is replaced with compound 717 in the preparation of compound 708: $^1$H NMR (500 MHz, CD$_3$OD) δ 8.7–8.6 (m), 8.6–8.4 (m), 8.1 (d), 8.0–7.8 (m), 7.6–7.5 (m), 7.5–7.4 (m), 7.2–7.0 (m), 7.0–6.9 (m), 5.5–5.3 (m), 5.3–5.2 (m), 4.6–4.5 (m), 4.5–4.3 (m), 4.2–4.0 (m), 3.8–3.6 (m), 3.3 (s), 3.2–3.1 (m), 3.1–3.0 (m), 3.0–2.8 (m), 2.7–2.6 (m), 2.4–2.0 (m), 1.2–0.6 (m).

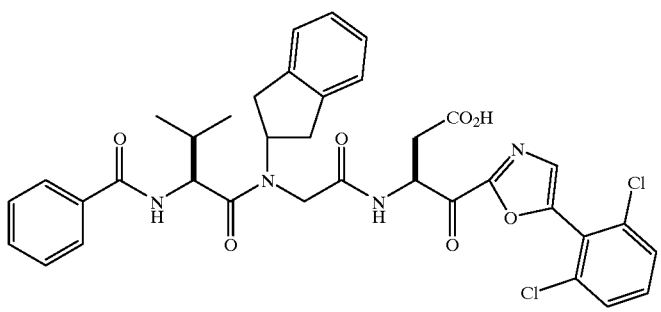

727

3(S)-(2-((2(S)-Benzoylamino-3-methylbutyryl)indan-2-ylamino)acetylamino)-4-(4-(3,5-dichlorophenyl)oxazol-2-yl)-4-oxobutyric Acid (727): Compound 727 was prepared by a method similar to the method use to prepare compound 710, except compound 704 is replaced with compound 724 in the preparation of compound 708: $^1$H NMR (500 MHz, CD$_3$OD) δ 8.73 (d), 8.38–8.21 (m), 8.20–8.11 (m), 7.81–7.72 (m), 7.50–7.32 (m), 7.14–6.93 (m), 5.52–5.40 (m), 5.22–5.13 (m), 5.08 (m), 4.96 (d), 4.56 (d), 4.48–4.37 (m), 4.21–4.10 (m), 3.98 (t), 3.82 (d), 3.26–3.11 (m), 3.10–2.88 (m), 2.25–2.12 (m), 1.04–0.83 (m).

3(S)-(2-((2(S)-((Benzo(1,3)dioxole-5-carbonyl)amino)-3-methylbutyryl)indan-2-yl amino)acetylamino)-4-(4-(3,5-dichlorophenyl)oxazol-2-yl)-4-oxobutyric Acid (729): Compound 729 was prepared by a method similar to the method used to prepare compound 710, except compound 704 is replaced with compound 728 in the preparation of 708: $^1$H NMR (500 MHz, CD$_3$OD) δ 8.36 (m), 8.22–8.03 (m), 7.58–7.37 (m), 7.36–7.23 (m), 7.22–7.01 (m), 6.89 (m), 6.00 (s), 5.51 (m), 5.29–5.04 (m), 4.97 (d), 4.61–4.49 (m), 4.48–4.31 (m), 4.27–4.19 (m), 4.09–3.78 (m), 3.28–3.39 (m), 3.18–2.93 (m), 2.90–2.59 (m), 2.51 (m), 2.22 (m), 1.12–0.83 (m).

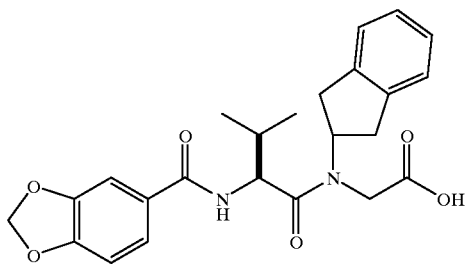

728

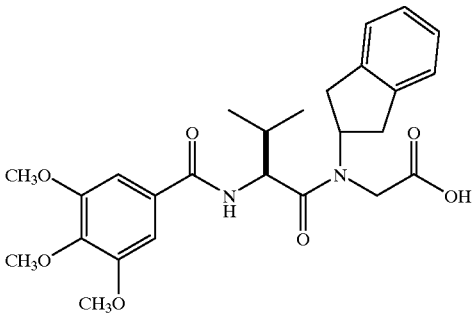

730

((2(S)-Benzo(1,3)dioxole-5-carbonylamino-3-methylbutyryl)indan-2-ylamino)acetic Acid (728): Compound 728 was prepared by a method similar to the method used to prepare compound 724, except benzoic acid is replaced with piperonylic acid in the preparation of compound 723.

((2(S)-(3,4,5-Trimethoxybenzoylamino)-3-methylbutyryl)indan-2-ylamino)acetic Acid (730): Compound 730 was prepared by a method similar to the method used to prepare compound 724, except benzoic acid is replaced with 3,4,5-trimethoxybenzoic acid in the preparation of 723.

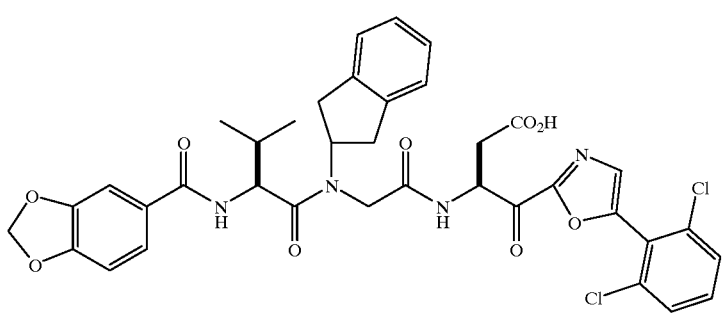

729

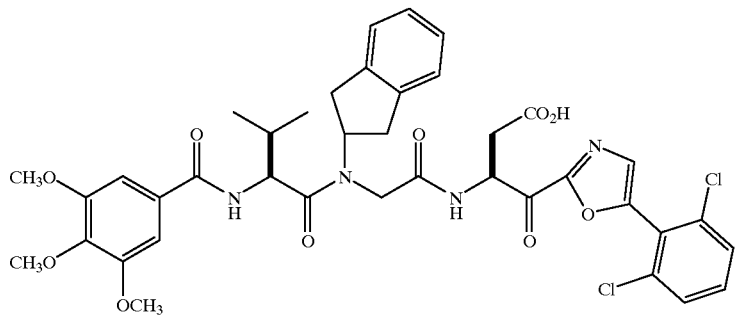

731

3(S)-(2-((2(S)-(3,4,5-Trimethoxybenzoylamino)-3-methylbutyryl)indan-2-yl amino)acetylamino)-4-(4-(3,5-dichlorophenyl)oxazol-2-yl)-4-oxobutyric Acid (731): Compound 731 was prepared by a method similar to the method used to prepare compound 710, except compound 704 is replaced with compound 730 in the preparation of 708: $^1$H NMR (500 MHz, CD$_3$OD) δ 8.51–8.32 (m), 8.31–8.22 (m), 7.60–7.03 (m), 5.62–5.49 (m), 5.32–5.02 (m), 4.97 (m), 4.64–4.53 (m), 4.48–4.21 (m), 4.09–3.72 (m), 3.28–2.89 (m), 2.85–2.42 (m), 2.25 (m), 1.38–1.24 (m), 1.11–0.83 (m).

3S)-(2-((2(S)-(4-Chlorobenzoylamino)-3-methylbutyryl)indan-2-yl amino)acetylamino)-4-(4-(3,5-dichlorophenyl)oxazol-2-yl)-4-oxobutyric Acid (733): Compound 33 was prepared by a method similar to the method used to prepare compound 710, except compound 704 is replaced with compound 732 in the preparation of 708: $^1$H NMR (500 MHz, CD$_3$OD) δ 8.99, 6.4–6.2 (m), 5.8–6.0 (m), 5.7–5.4 (m), 4.0–3.9 (m), 3.7–3.6 (m), 3.6–3.5 (m), 3.5–3.4 (m), 3.4–3.2 (m), 3.0 (m), 2.8 (m), 2.7 (m), 2.5–2.3 (m), 1.8–1.6 (m), 1.3–1.6 (m), 1.2 (m), 0.6 (m).

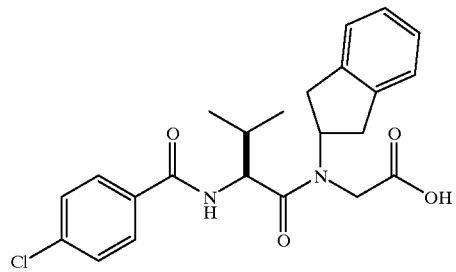

732

((2(S)-(3,4,5-Trimethoxybenzoylamino)-3-methylbutyryl)indan-2-ylamino)acetic Acid (732): Compound 732 was prepared by a method similar to the method used to prepare compound 724, except benzoic acid is replaced with 4-chlorobenzoic acid in the preparation of 723.

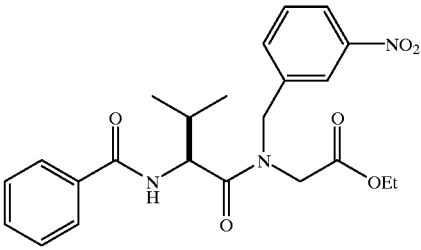

734

((2(S)-Benzoylamino-3-methylbutyryl)-(3-nitrobenzyl)amino)acetic Acid Ethyl Ester (734): Compound 734 was prepared by a method similar to the method used to prepare compound 703 except benzaldehdye was replaced with 3-nitrobenzaldehyde in the preparation of 701.

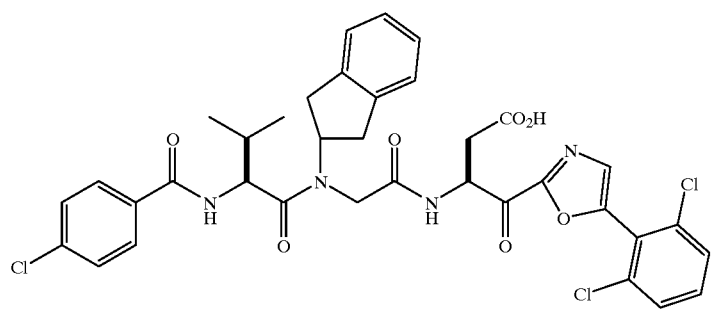

733

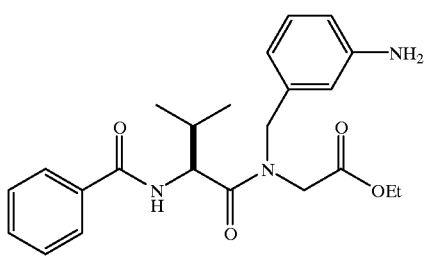

735

((2(S)-Benzoylamino-3-methylbutyryl)-(3-aminobenzyl) amino)acetic Acid Ethyl Ester (735): A mixture of compound 734 (1.5 g, 3.4 mmol) and 10% Pd/C (150 mg) in MeOH (35 mL) was placed under $H_2$ (1 atm) and stirred until the reduction was complete. The $H_2$ was replaced with nitrogen and the reaction filtered. The filtrate was concentrated to provide 1.38 g of compound 735.

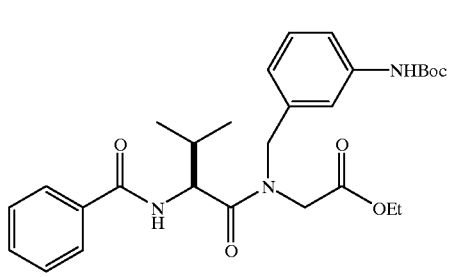

736

((2(S)-Benzoylamino-3-methylbutyryl)-(3-Bocaminobenzyl)amino)acetic Acid Ethyl Ester (703): To a solution of compound 735 (1.45 g, 3.5 mmol) and DIEA (740 µl, 4.25 mmol) in $CH_2Cl_2$ (7.0 mL) containing a catalytic amount of N,N-dimethylaminopyridine, was added di-tert-butyldicarbonate (850 mg, 3.9 mmol). After 1 hr, the reaction was diluted with EtOAc, washed with $H_2O$, sat. aq. $KHSO_4$, brine, dried over $MgSO_4$, filtered and concentrated in vacuo to provide 1.78 g of compound 736.

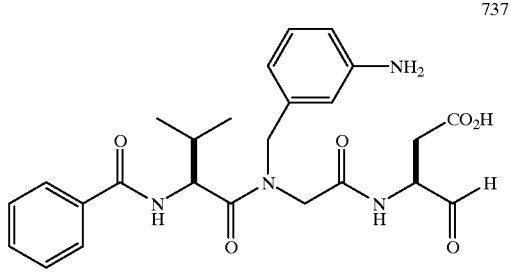

737

3(S)-(2-((2(S)-Benzoylamino-3-methylbutyryl)-(3-aminobenzyl)amino)acetylamino)-4-oxo-butyric Acid (737): Compound 737 was prepared by a method similar to the method used to prepare compound 706, except compound 703 was replaced with compound 736.

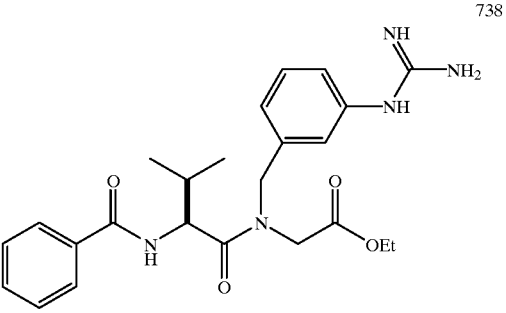

738

((2(S)-Benzoylamino-3-methylbutyryl)-(3-guanidionbenzyl)amino)acetic Acid Ethyl Ester (738): Compound 738 was prepared by a method similar to the method used to prepare compound 742.

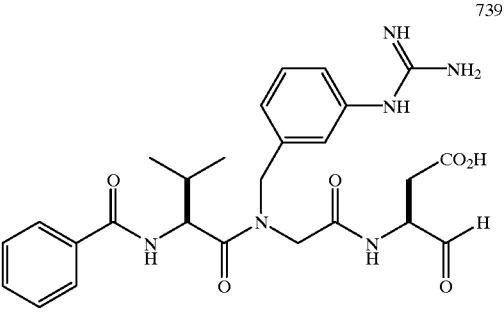

739

3(S)-(2-((2(S)-Benzoylamino-3-methylbutyryl)-(3—guanidionbenzyl)amino) acetylamino)-4-oxo-butyric Acid (739): Compound 739 was prepared by a method similar to the method used to prepare compound 706, except compound 703 was replaced with compound 738.

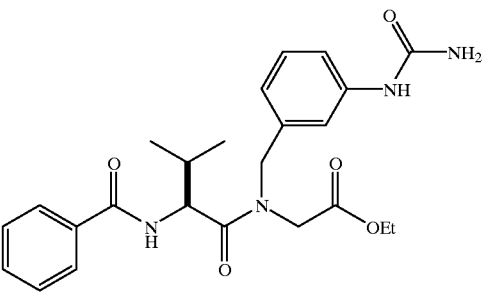

740

((2(S)-Benzoylamino-3-methylbutyryl)-(3-ureidobenzyl) amino)acetic Acid Ethyl Ester (740): Compound 740 was prepared by method similar to the method used to prepare compound 742.

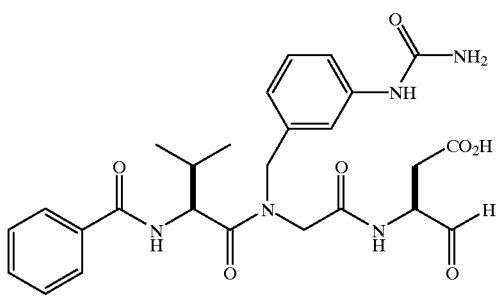

741

3(S)-(2-((2(S)-Benzoylamino-3-methylbutyryl)-(3-ureidobenzyl)amino)acetylamino)-4-oxo-butyric Acid (741): Compound 741 was prepared by a method similar to the method used to prepare compound 706, except compound 703 was replaced with compound 740.

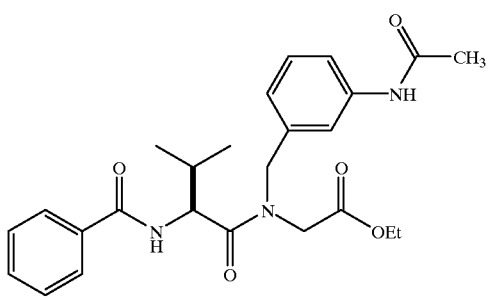

742

(3-Acetylaminobenzyl- (2(S)-benzoylamino-3-methylbutyryl)-amino)acetic Acid Ethyl Ester (742): To a solution of 735 (435.0 mg, 1.06 mmol) in pyridine (3.0 ml) was added acetic anhydride (50 μL, 1.59 mmol) and the reaction allowed to stir overnight. The reaction was diluted with EtOAc and 1N HCl. The layers were separated and the organic phase washed with brine, dried over MgSO$_4$, filtered and concentrated to dryness to provide 480 mg of 742.

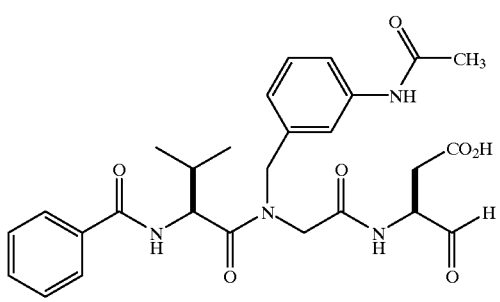

743

3(S)-(2-((3-Acetylaminobenzyl)-(2(S)-benzoylamino-3-methylbutyryl)amino)acetyl amino)-4-oxo-butyric Acid (743): Compound 743 was prepared by a method similar to the method used to prepare compound 706, except compound 703 was replaced with compound 742. $^1$H NMR (CD$_3$OD) δ 8.31–8.27 (m), 7.82–7.73 (m), 7.51–7.36 (m), 7.28–7.13 (m), 6.99 (d), 6.91 (d), 4.96–4.69 (m), 4.66–4.46 (m), 4.37–4.28 (m), 4.11–3.98 (t), 3.97–3.89 (n), 3.31–3.19 (m), 2.67–2.52 (m), 2.48–2.32 (m), 2.0 (d), 1.01–0.86 (m).

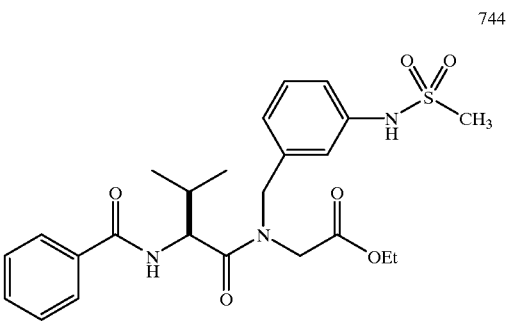

744

((2(S)-Benzoylamino-3-methylbutyryl)-(3-methanesulfonylbenzyl)amino)acetic Acid Ethyl Ester (744): To a solution of 735 (476.0 mg, 1.16 mmol) in pyridine (3.0 mL) was added methanesulfonyl chloride (135 μL, 1.75 mmol), and the reaction allowed to stir overnight. The reaction was diluted with EtOAc and 1N HCl. The layers were separated and the organic phase washed with brine, dried over MgSO$_4$, filtered and concentrated to provide 550 mg of 744.

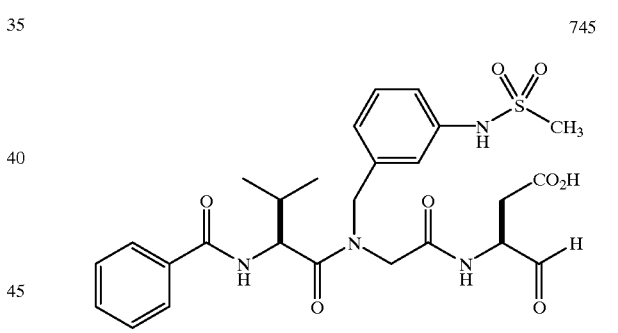

745

3(S)-(2-((2(S)-Benzoylamino-methylbutyryl)-(3-methanesulfonylbenzyl) amino)acetylamino)-4-oxo-butyric Acid (745): Compound 745 was prepared by a method similar to the method used to prepare compound 706, except compound 703 was replaced with compound 744. $^1$H NMR (CD$_3$OD) δ 8.29 (m), 8.02 (m), 7.82–7.69 (m), 7.51–7.32 (m), 7.29–7.01 (m), 6.98 (d), 4.94–4.38 (m), 4.36 (d), 4.34 (d), 4.30–4.13 (m), 4.04 (d), 3.31–3.19 (m), 2.88–2.77 (m), 2.64–2.48 (m), 2.44–2.32 (m), 2.21 (m), 1.00–0.83 (m).

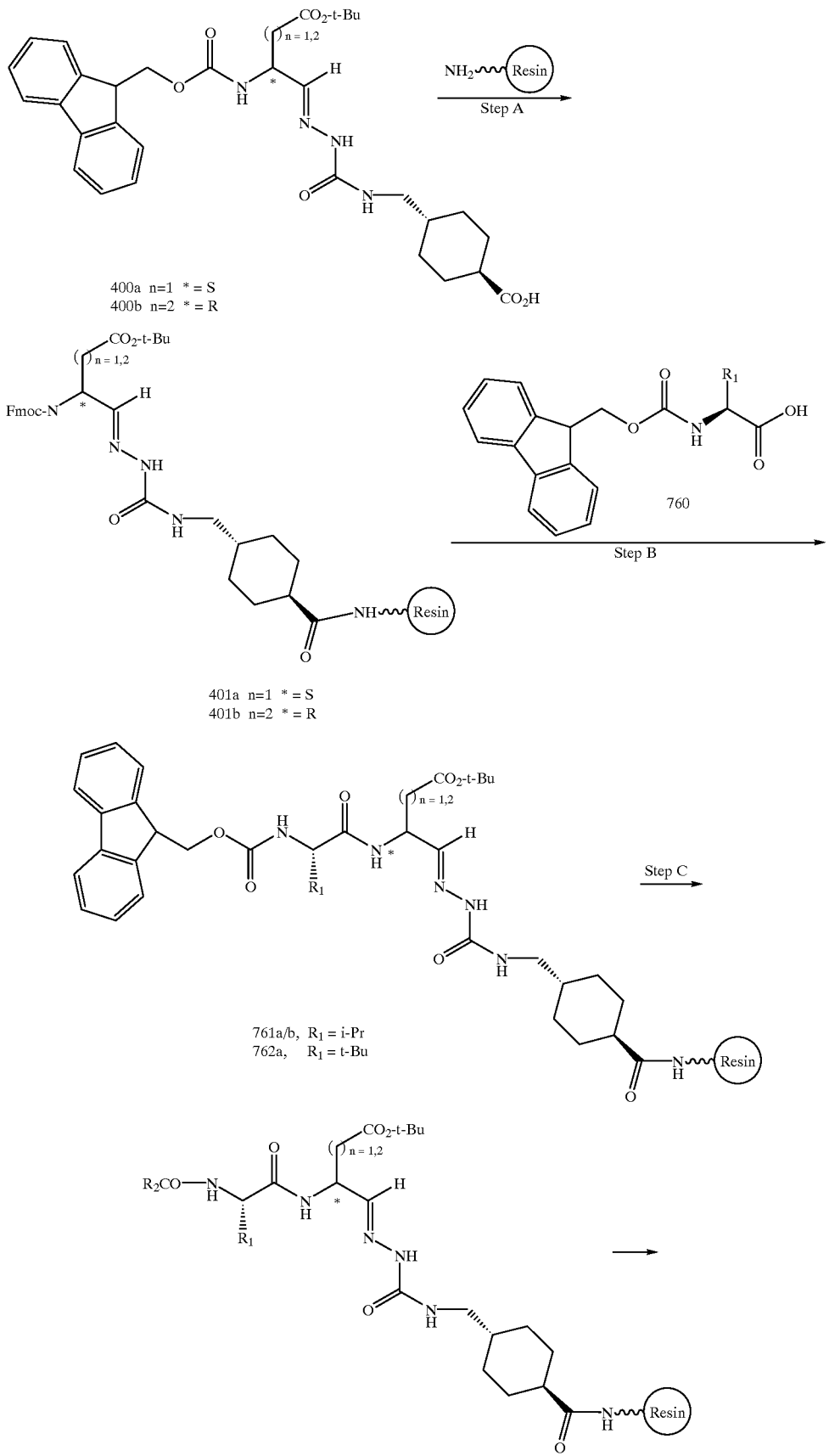

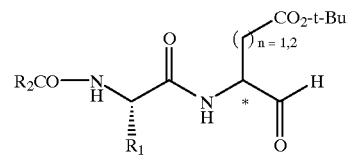

746-755

Step A. Synthesis of 401 a/b. TentaGel S® NH₂ resin (0.16 mmol/g, 10.0 g) was placed in a sintered glass funnel and washed with DMF (3×50 mL), 10% (v/v) DIEA in DMF (2×50 mL) and finally with DMF (4×50 mL). Sufficient DMF was added to the resin to obtain a slurry followed by 713a (1.42 g, 2.4 mmol, prepared from either (3S) 3-(fluorenylmethyloxycarbonyl)-4-oxobutryic acid t-butyl ester according to A. M. Murphy et al. *J. Am. Chem. Soc.*, 114, 3156–3157 (1992)) or 713b (1.42 g, 2.4 mmol, prepared from (3R) 3-(fluorenylmethyloxycarbonyl)-4-oxopentanoic acid t-butyl ester according to A. M. Murphy et al. *J. Am. Chem. Soc.*, 114, 3156–3157 (1992)), HOBT (HOBT.H₂O; 0.367 g 2.4 mmol), O-benzotriazole-N,N,N,N'-tetramethyluronium hexafluorophosphate (HBTU; 0.91 g 2.4 mmol), and DIEA (0.55 mL, 3.2 mmol). The reaction mixture was agitated overnight at rt using a wrist arm shaker. The resin was isolated on a sintered glass funnel by suction filtration and washed with DMF (3×50 mL). Unreacted amine groups were then capped by reacting the resin with 20% (v/v) acetic anhydride/DMF (2×25 mL) directly in the funnel (10 min/wash). The resin was washed with DMF (3×50 mL) and CH₂Cl₂ (3×50 mL) prior to drying overnight in vacuo.

Step B. Method 1: Synthesis of 761a/b and 762a. Resins 761a and 762a were prepared from resin 401a (0.24 g, 0.038 mmol) and Fmoc-Valine or Fmoc-t-Leucine, respectively, while resin 761b was prepared from resin 401b and Fmoc-Valine using an Advanced ChemTech 396 Multiple Peptide synthesizer. The automated cycles consisted of a resin wash with DMF (3×1 mL), deprotection with 25% (v/v) piperidine in DMF (1 mL) for 3 min followed by fresh reagent (1 mL) for 10 min. The resin was washed with DMF (3×1 mL) and N-methypyrrolidone (3×1 mL). The resin was then acylated with a solution of either 0.4M Fmoc-1-Valine or Fmoc-t-Leucine and 0.4M HOBT in N-methypyrrolidone (1 mL), a solution of 0.4M HBTU in N-methypyrrolidone (0.5 mL) and a solution of 1.6M DIEA in N-methypyrrolidone (0.35 mL) and the reaction was shaken for 2 hr at rt. The acylation step was repeated. Finally, the resins were washed with DMF (3×1 mL).

Step C. Method 1. Synthesis of 747, 748, 752, 753, and 755. The appropriate carboxylic acid (0.4M in 0.4 M HOBt/ITP) was coupled to the resin as described in Step B. The aldehyde was cleaved from the resin and globally deprotected by treatment with 95% TFA/5% H₂O (v/v, 1.5 mL) for 30 min at rt. After washing the resin with cleavage reagent (1 mL), the a combined filtrates were added to cold 1:1 Et₂O:pentane (12 mL) and the resulting precipitate was isolated by centrifugation and decantation. The resulting pellet was dissolved in 10% CH₃CN/90% H₂O/0.1% TFA (15 mL) and lyophilized to obtain the crude product as a white powder. The compound was purified by semi-prep RP-HPLC with a Rainin Microsorb™ C18 column (5 μ, 21.4×250 mm) eluting with a linear CH₃CN gradient (10%–60%) containing 0.1% TFA (v/v) over 45 min at 12 mL/min. Fractions containing the desired product were pooled and lyophilized.

Step C. Method 1A. Synthesis of 751. Following a similar procedure as method 1, resin 761a was acylated with 4-(1-fluorenylmethoxycarbonylamino)benzoic acid and repeated. The Fmoc group was removed as described in Step C and the free amine was acetylated with 20% (v/v) acetic anhydride in DMF (1 mL) and 1.6M DIEA in N-methylpyrrolidone (0.35 mL) for 2 hr at rt. The acetylation step was repeated. Cleavage of the aldehyde from the resin gave 751.

Analytical HPLC methods:

(1) Waters DeltaPak C18, 300A (5 μ, 3.9×150 mm). Linear CH₃CN gradient (10%–60%) containing 0.1% TFA (v/v) over 14 min at 1 mL/min.

Compounds 746–755 were prepared from the following combinatorial methods.

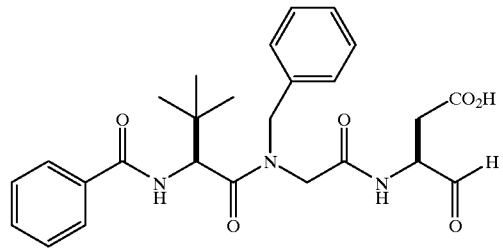

746

3(S)-(2-((2(S)-Benzoylamino-3,3-dimethylbutyryl) benzylamino)acetylamino)-4-oxo-butyric Acid (746): 0.7 mg (4%) as a white solid: Rt(1)=11.14 min (87%); (M+H)+= 482 (C₂₆H₃₁N₃O₆ requires 481.6).

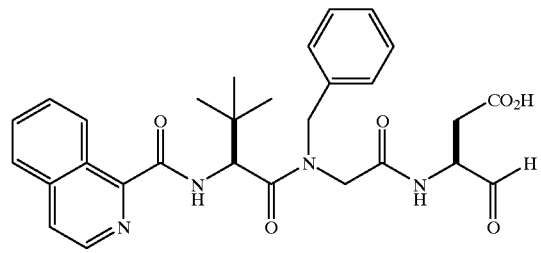

747

3(S)-(2(S)-(Benzyl-(2-((isoquinoline-1-carbonyl)amino)-3,3-dimethylbutyryl) amino)acetylamino)-4-oxo-butyric Acid (747): 2.0 mg (8%) as a white solid: Rt(1)=12.27 min (98%); (M+H)+=533 (C₂₉H₃₂N₄O₆ requires 532.6).

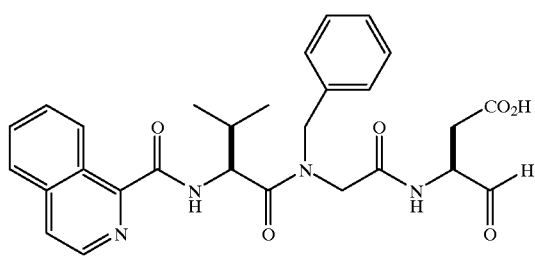

3(S)-(2(S)-(Benzyl-(2-((isoquinoline-1-carbonyl)amino)-3-methylbutyryl) amino)acetylamino)-4-oxo-butyric Acid (748): 9.2 mg (38%) as a white solid: Rt(1)=11.05 min (98%); (M+H)+=519 ($C_{28}H_{30}N_4O_6$ requires 518.6).

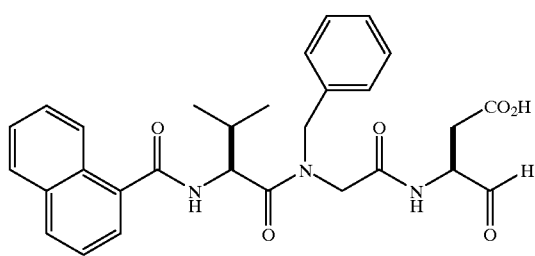

3(S)-(2(5)-(Benzyl-(2-((napthalene-1-carbonyl)amino)-3-methylbutyryl) amino)acetylamino)-4-oxo-butyric Acid (749): 7.9 mg (40%) as a white solid: Rt(1)=11.78 min (98%); (M+H)+=518 ($C_{29}H_{31}N_3O_6$ requires 517.6).

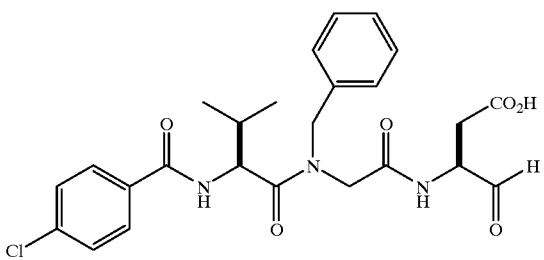

3(S)-(2-((2(S)-(4-Chlorobenzoyl)amino-3-methylbutyryl) benzylamino)acetylamino)-4-oxo-butyric Acid (750): 5.9 mg (31% as a white solid: Rt(1)=11.63 min (98%); (M+H)+=502 ($C_{25}H_{29}C_1N_3O_6$ requires 501.5).

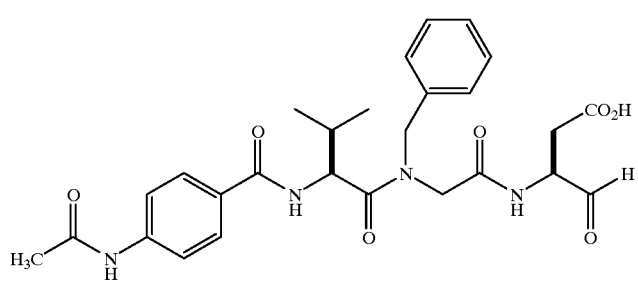

3(S)-(2-((2(S)-(4-Acetylaminobenzoyl) amino-3-methylbutyryl)benzylamino) acetylamino)-4-oxo-butyric Acid (751): 3.8 mg (19%) as a white solid: Rt(1)=8.50 min (98%); (M+H)+=525 ($C_{27}H_{32}N_4O_7$ requires 524.6).

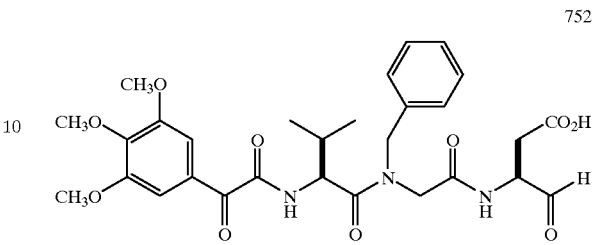

3(S)-(2(S)-(Benzyl(3-methyl-2-(2-oxo-2-(3,4,5-trimethoxyacetylamino)butyryl)amino)acetylamino)-4-oxo-butyric Acid (752): 5.0 mg (22%) as a white solid: Rt(1)= 11.09 min (97%); (M+Na)+=608 ($C_{29}H_{35}N_3O_{10}$ requires 585.6).

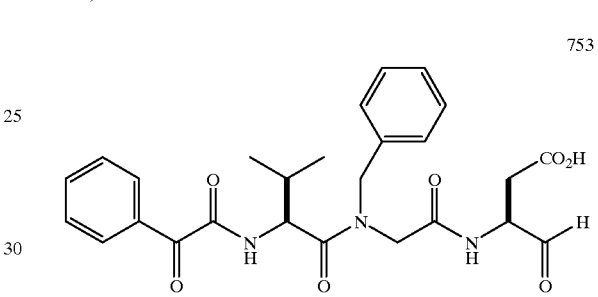

3(S)-(2(S)-(Benzyl(3-methyl-2-(2-oxo-2-phenylacetylamino)butyryl)amino) acetylamino)-4-oxo-butyric Acid (753): 3.0 mg (16%) as a white solid: Rt(1)=11.02 min (96%); (M+Na)+=518 ($C_{26}H_{29}N_3O_7$ requires 495.5).

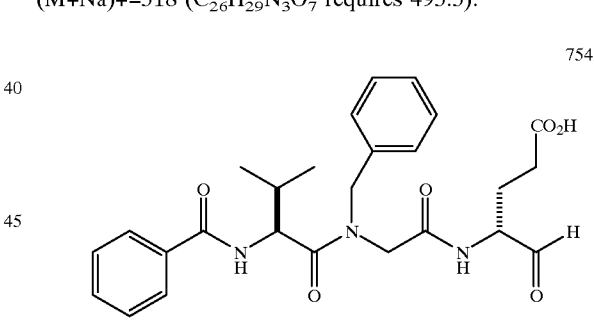

4(R)-(2(S)-((2-Benzoylamino-3-methylbutyryl)benzyl-amino)acetylamino)-5-oxopentanoic Acid (754): 3.5 mg (19%) as a white solid: Rt(1)=9.56 min (94%); (M+H)+=482 ($C_{26}H_{31}N_3O_6$ requires 481.6)

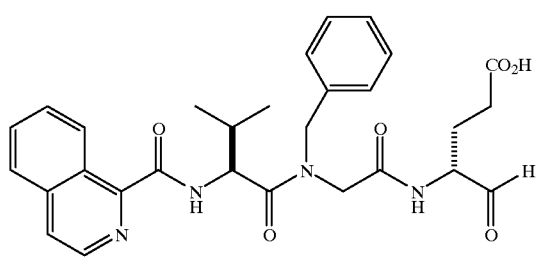

4(R)-(2(S)-(Benzyl-(2-((isoquinoline-1-carbonyl)amino)-3-methylbutyryl)amino) acetylamino)-5-oxopentanoic Acid (755): 6.0 mg (24%) as a white solid: Rt(1)=10.53 min (93%); (M+H)+=533 ($C_{29}H_{32}N_4O_6$ requires 532.6).

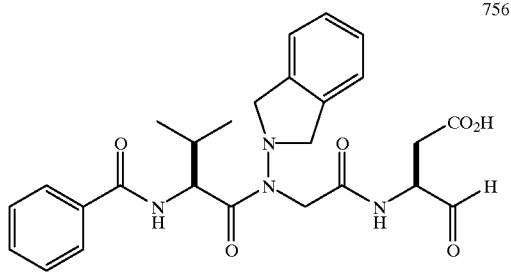

3(S)-(2-((2(S)-(Benzoyl)amino-3-methylbutyryl)-(1,3-dihydroisoindol-2-yl)amino)acetylamino)-4-oxo-butyric Acid (756): Compound 756 was prepared by a method similar to the method used to prepare compound 724 and compound 706, except 2-aminoindane was replaced with 2-aminoisoindoline (prepared as described in Eloy, F., Moussebois, C., *Bull. Soc. Chim. Bela.*, 68, pp. 409–421 (1959)).

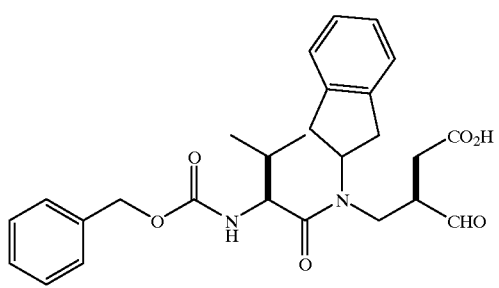

3(S)-(2-((2(S)-(benzyloxycarbonylamino-3-methylbutyryl)-indan-2-yl)amino)acetylamino)-4-oxobutyric acid (757): was prepared from ((2(S)- benzyloxycarbonyl-3-methylbutyryl) indan-2-yl)amino) acetic acid by a method similar to the preparation of 706: $^1$H NMR (CD$_3$OD) δ 7.4–7.5 (m), 7.1–7.2 (m), 5.0–5.2 (m), 4.8–4.95 (dd), 4.5–4.7 (m), 3.8–4.4 (m), 3.5 (m), 2.9–3.4 (m), 2.4–2.8 (m) 2.0–2.2 (m), 0.90–1.15 (m).

We claim:

1. A compound represented by the formula:

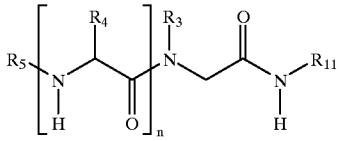

wherein:

n is 0, 1, or 2;

$R_{11}$ is:

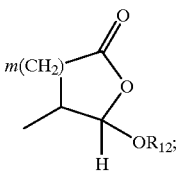

m is 1 or 2;

$R_{12}$ is selected from the group consisting of —$R_7$, —C(O)—$R_7$, and —C(O)—N(H)—$R_7$;

$R_7$ is selected from the group consisting of —Ar, a —$C_{1-6}$ straight or branched alkyl group optionally substituted with —Ar, a —$C_{1-6}$ straight or branched alkenyl group optionally substituted with Ar, and a —$C_{2-6}$ straight or branched alkynyl group optionally substituted with Ar;

$R_5$ is selected from the group consisting of:
—C(O)—$R_7$,
—C(O)—O$R_9$,
—C(O)—N($R_9$)($R_{10}$),
—S(O)$_2$—$R_7$,
—C(O)C(O)—$R_7$,
—$R_7$, and
—H;

each Ar is a cyclic group independently selected from the set consisting of phenyl, 1-naphthyl, 2-naphthyl, indenyl, azulenyl, fluorenyl and anthracenyl and a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, peridinyl, carbazolyl, acridinyl, phenazinyl, phenothiazinyl and phenoxazinyl, and the aromatic group is optionally singly or multiply substituted with —F, —Cl, —Br, —I, —O$R_{14}$, —NO$_2$, —S(O$_2$)—N($R_9$)($R_{10}$), —C(O)—N($R_9$)($R_{10}$), —N(H)—C(O)—N($R_9$)($R_{10}$), —N($R_9$)($R_{10}$), —C(O)—O$R_9$, —CF$_3$, —OCF$_3$, a $C_{1-6}$ straight or branched alkyl group, 1,2-methylenedioxy, —CN, or —N(H)C($_9$)N(R)($R_{10}$);

each $R_{14}$ is —H or a $C_{1-6}$ straight or branched alkyl group;

each $R_9$ and $R_{10}$ is independently selected from the group consisting of —H, —Ar, and a $C_{1-5}$ straight or branched alkyl group optionally substituted with —Ar;

each $R_4$ is a —$C_{1-5}$ straight or branched alkyl group optionally substituted with —Ar or —W;

W is —$OR_9$, —$SR_9$, —N(H)C(NR$_9$)N(R$_9$)(R$_{10}$), —C(O)—OR, or —N(R$_9$)(R$_{10}$);

$R_3$ is —CH$_2$Ar or

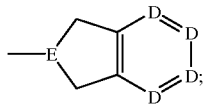

E is CH or N;

each D is independently N, CH, or C optionally substituted with —OR$_{14}$, —F, —Cl, —Br, —I, —NO$_2$, —S(O)$_2$—N(R$_9$)(R$_{10}$), —C(O)—N(R$_9$)(R$_{10}$), —N(H)—C(O)—N(R$_9$)(R$_{10}$)—N (R$_9$)(R$_{10}$)—C(O)—OR$_9$—CF$_3$, —OCF$_3$, a $C_{1-6}$ straight or branched alkyl group, 1,2-methylenedioxy, —CN, or —N(H)C(NR$_9$) N(R$_9$)(R$_{10}$);

provided that when —Ar is substituted with a group containing $R_9$ or $R_{10}$ which comprises one or more additional —Ar groups, the —Ar groups are not substituted with a group containing $R_9$ or $R_{10}$.

2. A compound according to claim 1, wherein:

$R_5$ is —C(O)—R$_7$ or —C(O)C(O)—R$_7$;

each $R_4$ is a $C_{1-5}$ straight or branched alkyl group optionally substituted with Ar;

m is 1;

n is 1;

each $R_9$ and $R_{10}$ is independently selected from the group consisting of —H, —Ar, and a —$C_{1-5}$ straight or branched alkyl group optionally substituted with —Ar.

3. A pharmaceutical composition comprising a compound according to any one of claims 1 or 2 in an amount effective for treating an IL-1-mediated disease and a pharmaceutically acceptable carrier.

4. A pharmaceutical composition comprising a compound according to any one of claims 1 or 2 in an amount effective for treating an apoptosis-mediated disease and a pharmaceutically acceptable carrier.

5. The pharmaceutical composition according to claim 3, wherein the IL-1-mediated disease is an inflammatory disease selected from the group consisting of osteoarthritis, pancreatitis, asthma, and adult respiratory distress syndrome.

6. The pharmaceutical composition according to claim 5, wherein the inflammatory disease is osteoarthritis or acute pancreatitis.

7. The pharmaceutical composition according to claim 3, wherein the IL-1-mediated disease is an autoimmune disease selected from the group consisting of glomeralonephritis, rheumatoid arthritis, systemic lupus erythematosus, scleroderma, chronic thyroiditis, Grave's disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, and graft vs host disease.

8. The pharmaceutical composition according to claim 7, wherein the autoimmune disease is rheumatoid arthritis, inflammatory bowel disease, Crohn's disease, or psoriasis.

9. The pharmaceutical composition according to claim 3, wherein the IL-1-mediated disease is a bone destructive disorder, wherein the disorder is osteoporosis or a multiple myeloma-related bone disorder.

10. The pharmaceutical composition according to claim 3, wherein the IL-1-mediated disease is a proliferative disorder selected from the group consisting of acute myelogenous leukemia, chronic myelogenous leukemia, metastatic melanoma, Kaposi's sarcoma, and multiple myeloma.

11. The pharmaceutical composition according to claim 3, wherein the TL-1-mediated disease is an infectious disease, selected from the group consisting of sepsis, septic shock, and Shigellosis.

12. The pharmaceutical composition according to claim 3, wherein the IL-1-mediated disease is a degenerative or necrotic disease, selected from the group consisting of Alzheimer's disease, Parkinson's disease, cerebral ischemia, and myocardial ischemia.

13. The pharmaceutical composition according to claim 12, wherein the degenerative disease is Alzheimer's disease.

14. The pharmaceutical composition according to claim 4, wherein the apoptosis-mediated disease is a degenerative disease, selected from the group consisting of Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

15. A pharmaceutical composition for inhibiting an ICE-mediated function comprising a compound according to any one of claims 1 or 2, and a pharmaceutically acceptable carrier.

16. A method for treating a disease selected from the group consisting of an IL-1-mediated disease, an apoptosis mediated disease, an inflammatory disease, an autoimmune disease, a proliferative disorder, an infectious disease, a degenerative disease, a necrotic disease, osteoarthritis, pancreatitis, asthma, adult respiratory distress syndrome, glomeralonephritis, rheumatoid arthritis, systemic lupus erythematosus, scleroderma, chronic thyroiditis, Grave's disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, graft vs host disease, osteoporosis, multiple myeloma-related bone disorder, acute myelogenous leukemia, chronic myelogenous leukemia, metastatic melanoma, Kaposi's sarcoma, multiple myeloma, sepsis, septic shock, Shigellosis, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke in a patient comprising the step of administering to said patient a pharmaceutical composition according to any one of claims 3 to 15.

* * * * *